United States Patent [19]
Dodd et al.

[11] Patent Number: 5,834,521
[45] Date of Patent: *Nov. 10, 1998

[54] SUBSTITUTED DIBENZ (A F)AZULENES AND METHODS OF PREPARATION

[75] Inventors: John H. Dodd, Pittstown; Lisa A. Dixon, Somerville; James L. Bullington, Hamilton Square; Charles F. Schwender, Califon, all of N.J.

[73] Assignee: Ortho Pharmaceutical Corporation, Raritan, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 693,861

[22] Filed: Aug. 5, 1996

Related U.S. Application Data

[63] Continuation of Ser. No. 401,603, Mar. 9, 1995, abandoned.

[51] Int. Cl.⁶ ........................ A61K 31/015; A61K 31/09; C07C 13/66
[52] U.S. Cl. .......................... 514/765; 514/381; 514/546; 514/625; 514/656; 514/718; 514/717; 514/721; 514/729; 514/753; 514/680; 548/251; 560/129; 560/190; 562/8; 564/221; 564/222; 564/426; 568/326; 568/632; 568/633; 568/808; 574/123; 574/183; 585/26; 585/27
[58] Field of Search ..................................... 564/192, 221, 564/258, 270, 222, 385, 391, 415, 416, 426; 514/625, 510, 753, 765, 381, 546, 656, 718, 717, 721, 729; 560/56, 129, 190; 568/309, 316, 326, 632, 633, 808; 562/8; 570/123, 183; 585/26, 27

[56] References Cited

PUBLICATIONS

Koppes et al, Recl. Trav. Chim. Days—Bas, 549–62, 1988.
Korth et al, J. Am. Chem. Soc., 2767–2777, 1994.
Sasaki et al, Chem. Pharm. Bull., 2868–2878, 1983.

*Primary Examiner*—Shailendra Kumar

[57] ABSTRACT

Tetracyclic compounds having the following structure are described:

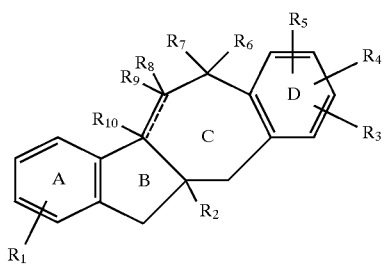

wherein $R_1$–$R_{10}$ are as defined. The tetracyclic compounds are capable of potent effects on steroid sensitive tissues and have demonstrated increased uterine weight, antiovulatory effects and potent steroid receptor binding. The compounds have therapeutic utility in reproductive applications such as fertility control, labor induction, ovulation induction and spermatogenesis. Methods for preparing the tetracyclic compounds from substituted indanones are also described.

12 Claims, No Drawings

SUBSTITUTED DIBENZ (A F)AZULENES AND METHODS OF PREPARATION

This is a continuation of application Ser. No. 08/401,603, filed Mar. 9, 1995, abandoned.

FIELD OF THE INVENTION

The present invention relates to novel chemical compounds of the following formula:

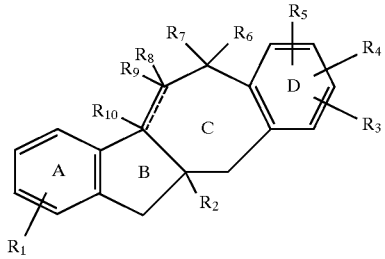

wherein
- $R_1$ is selected from the group consisting of hydrogen, halo, alkoxy ($C_1$–$C_6$) and hydroxy;
- $R_2$ is alkyl ($C_1$–$C_6$);
- $R_3$, $R_4$ and $R_5$ are selected from the group consisting of hydrogen, alkyl ($C_1$–$C_6$), alkoxy ($C_1$–$C_6$), benzyloxy, acyl ($C_2$–$C_6$), acyloxy ($C_2$–$C_6$), alkoxycarboxy wherein the alkoxy group has 1–5 carbon atoms, amino, acylamino ($C_2$–$C_6$), halo, nitro, hydroxy, cyano, alkylaminoalkoxy wherein the alkyl and alkoxy groups each contain 1–5 carbons, nitroso, dialkylphosphoryloxy, hydroxyalkyl ($C_1$–$C_6$), and phenyltetrazoyloxy;
- $R_6$ and $R_7$ are selected from hydrogen, alkyl ($C_1$–$C_6$), hydroxy, and when taken together alkylene ($C_1$–$C_6$) and carbonyl;
- $R_8$ is selected from hydrogen, alkyl, hydroxy or acyloxy ($C_2$–$C_6$);
- $R_9$ and $R_{10}$ are hydrogen or together form a double bond, and $R_8$ and $R_9$ taken together form a carbonyl group, when $R_{10}$ is hydrogen.

For the purpose of this invention, alkyl is defined as 1–6 carbons straight, branched or cyclic; halogen refers to fluorine, chlorine, bromine or iodine; alkoxy refers to groups derived from alcohols with straight or branched carbon chains having 1–4 carbons; acyloxy is defined as groups derived from aliphatic acids with straight or branched carbon chains having 2–6 carbons; alkenyl is defined as straight, branched or cyclic groups having 1–5 carbons which contain 1–4 degrees of unsaturation. All diastereomers which result from reduction of double bonds in the compounds as well as the substituents are included in this invention. The enantiomers of all possible diastereomers are also included in this invention.

The compounds of this invention are capable of potent effects on steroid sensitive tissues and have demonstrated increased uterine weight, antiovulatory effects and potent steroid receptor binding. The compounds of this invention have therapeutic utility in reproductive applications such as fertility control, labor induction, ovulation induction, and spermatogenesis. In addition to their reproductive uses, the compounds of this invention can be expected to find utility in the treatment of progestin mediated maladies such as osteoporosis, hormone dependent carcinomas, uterine fibroids, precocious puberty, endometriosis, inflammatory dermatosis, arthritis, systemic lupus erythematosis, multiple sclerosis, type I diabetes, drug hypersensitivity, bronchial asthma, status asthmatics, allergic rhinitis, graft versus host disease and ulcerative colitis.

DESCRIPTION OF THE PRIOR ART

The novelty of this invention resides in the non-steroidal structure of the compounds and their steroid-mimetic behavior. Structurally, the compounds are tetracycles, where the first and the fourth rings are aromatic, six membered carbocycles, the second ring is a five membered carbocyclic ring, and the third ring is a seven membered carbocyclic ring wherein the degree of saturation varies. The compounds have an alkyl substituent at the ring junction of the second and the third ring.

The prior art closest to the claimed compounds includes the following:

1. Homo-27-3,4-secogammacer-4(23)-enes;

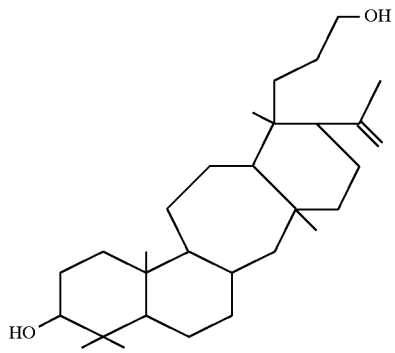

Y. Tsuda, T. Fujimoto, A. Morimoto, T. Sano, *Chem. Pharm. Bull.* 1975, 23 (6) 1336–46;

2. Dibenz[a,f]azulene-5(6H)-ones;

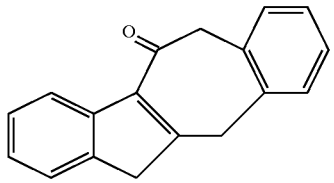

H. Sasaki, T. Kitagawa, *Chem. Pharm. Bull.* 1983, 31 f(8), 2868–78;

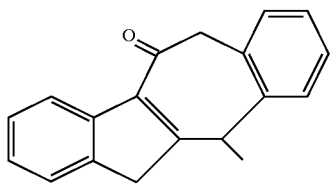

M. Koppes, H. Cerfontain, *Recl. Trav. Chim. Pays-Bas,* 1988, 107 (9), 549–62.

3. Dibenz[a,f]azulenes;

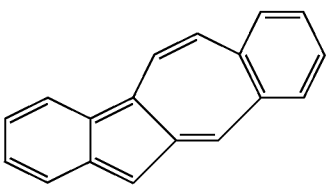

Z. Chen, *Shanxi Daxue Xuebao, Ziran Kexueban*, 1985, 30, 53–65;

DETAILED DESCRIPTION OF THE INVENTION

The invention relates to a novel series of tetracycles the pharmacological activity of which mimics that of a number of naturally occurring steroids, i.e. progestins and estrogens. Several of the intermediates formed in the preparation of the compounds of this invention as well as the processes of preparing them are novel and are considered to be part of the invention.

The preferred compounds of the invention are those wherein $R_1$ is selected from the group consisting of hydrogen, halo, alkoxy and hydroxy; $R_2$ is alkyl; $R_3$, $R_4$ and $R_5$ are selected from the group consisting of hydrogen, alkyl, alkoxy, benzyloxy, acyl, acyloxy, amino, acylamino, halo, nitro, hydroxy, and alkylaminoalkoxy; $R_6$ and $R_7$ are hydrogen, alkyl, alkylene, hydroxy or carbonyl; $R_8$ is hydrogen, hydroxy or acyloxy; and $R_9$ and $R_{10}$ are hydrogen or together form a double bond.

The tetracycles of this invention are prepared as outlined in the reaction scheme described below. As can be seen from the reaction scheme, an appropriately substituted indanone (I), wherein $R_1$ is hydrogen, halogen or alkoxy; $R_2$ is a straight or branched chain alkyl group and $R_3$, $R_4$ and $R_5$ are straight or branched chain alkyl, acylamino, alkoxy or hydroxy, is reacted with an appropriately substituted metal halide such as, for example, allylmagnesium bromide, vinyllithium or vinylmagnesium bromide and crotyl magnesium bromide, in a suitable solvent such as tetrahydrofuran (THF), diethyl ether or diisopropyl ether to give the substituted azulenes IIa and IIb (compound II). The reaction is generally carried out at a temperature between −78 degrees centigrade and room temperature for about 1–5 hours. The intermediate 2,3-dihydroindan-1-ol which forms is then reacted with a cyclizing agent such as p-toluenesulfonic acid or camphorsulfonic acid in a suitable solvent such as toluene, benzene or xylene or with thionyl chloride in a suitable solvent such as carbon tetrachloride, chloroform or methylene chloride to give compounds IIa and IIb. In the above reaction scheme at least one of $R_3$, $R_4$ and $R_5$ must be in the meta position relative to the methylene connecting group and be an electron donating group. $R_6$, $R_7$ and $R_8$ in azulenes IIa and IIb will be hydrogen or alkyl, depending upon the particular organometallic compound employed. The mixture of azulenes IIa and IIb can be separated by techniques known to those skilled in the art such as, for example, chromatography and crystallization.

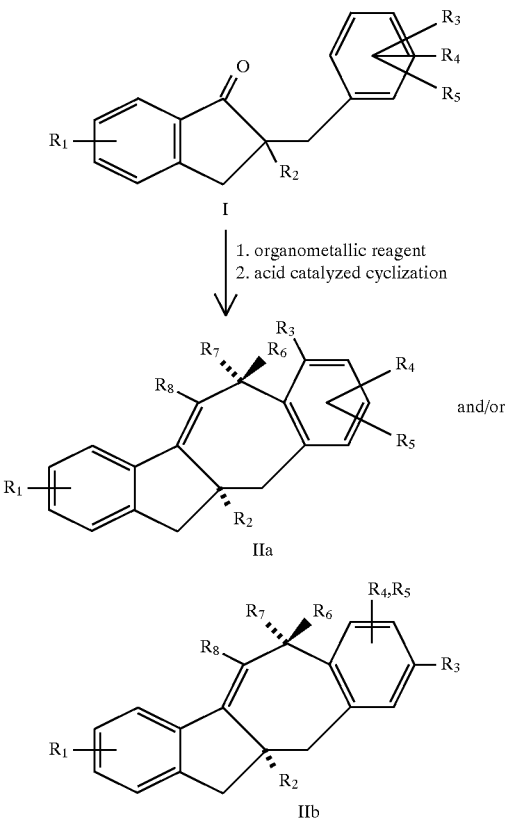

Reduction of azulenes IIa and IIb with hydrogen in the presence of a catalyst such as palladium on carbon, palladium on calcium carbonate or palladium hydroxide on carbon in a suitable solvent such as ethyl acetate, ethanol, methanol or THF yields a mixture of diastereomeric derivatives IIIa and IIIb. The hydrogenation step is generally carried out at room temperature at approximately 30–50 psi. The diastereomeric derivatives can be separated by techniques known to those skilled in the art such as chromatography and crystallization, for example.

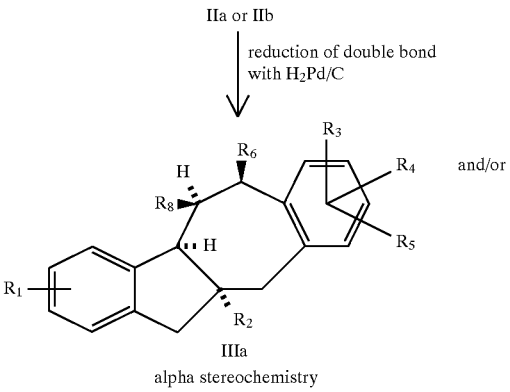

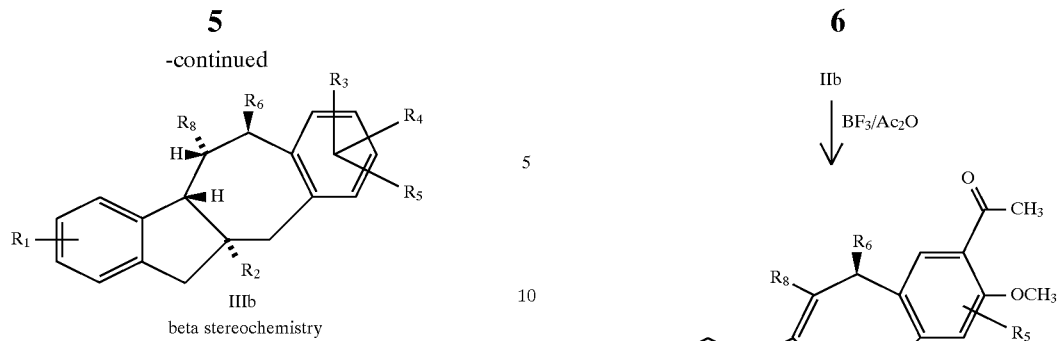

IIIb
beta stereochemistry

The alpha derivative is the stereoisomer wherein the hydrogen atoms are on the same side of the molecule as $R_2$; the beta derivative is the stereoisomer wherein the hydrogen atoms are on the side opposite from $R_2$ of the molecule. The alpha and beta isomers are obtained in the reaction. The alpha isomer, unless otherwise indicated, is the isomer that is illustrated in the scheme from this point on, even though all of the following transformations can be performed on both the alpha and beta isomers.

Those compounds of derivative IIIa wherein $R_3$ is methoxy or benzyloxy and $R_1$ is hydrogen, hydroxy or halogen are reacted with boron tribromide in a suitable solvent such as methylene chloride, hexane or cyclohexane to yield the corresponding phenol (VI). Acylation of the phenol (VI) with an acid anhydride such as acetic anhydride or an acyl halide such as acetyl chloride in a suitable solvent such as chloroform, methylene chloride or THF yields the corresponding ester (VII). Esters can also be prepared from compounds IIa and IIb wherein $R_3$ is hydroxy by similar acylation methods.

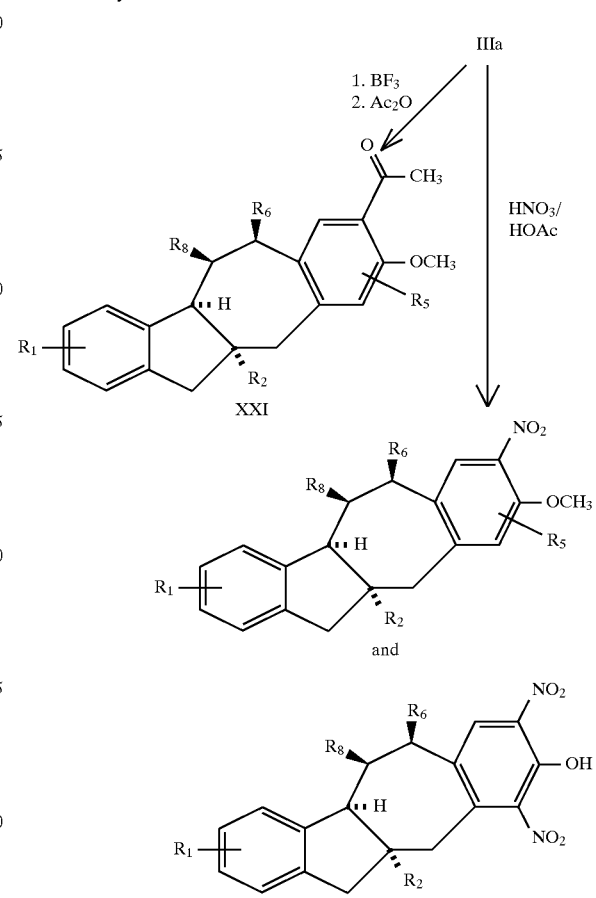

Reaction of compound IIb, wherein $R_3$ is alkoxy or $NHCOCH_3$ and $R_1$ is hydrogen or halogen, with boron trifluoride in the presence of an anhydride, such as acetic anhydride or propionic anhydride, results in the formation of the corresponding compounds (XX) wherein $R_4$ is acyl.

Reaction of compound IIIa, wherein $R_3$ is alkoxy or acetamido and $R_1$ is hydrogen or halo, with a nitrating agent such as, for example, nitric acid in the presence of acetic acid in a suitable solvent such as acetic acid or propionic acid, results in the formation of those compounds wherein $R_4$ is nitro. In the mono- or di-nitration step, where $R_3$ is alkoxy, the loss of the alkyl group can occur to form the phenol, depending upon the reaction conditions. The alkyl ketones (XXI) can be prepared from compound IIIa by reaction with boron trifluoride and an acid anhydride such as acetic anhydride.

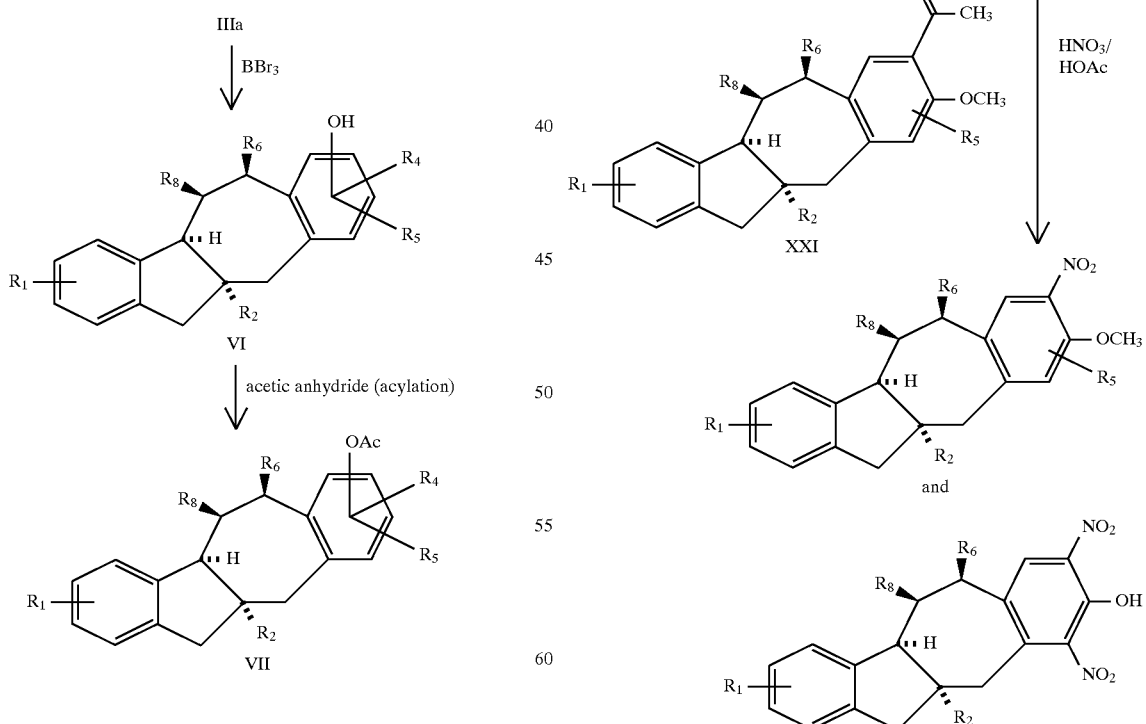

Reaction of compound IIa, wherein $R_3$ is acylamino, with a mineral acid, such as hydrochloric acid, hydrobromic acid or dilute sulfuric acid, in a suitable solvent such as methanol, ethanol, propanol or butanol, results in the corresponding compounds (IX) wherein $R_3$ is amino.

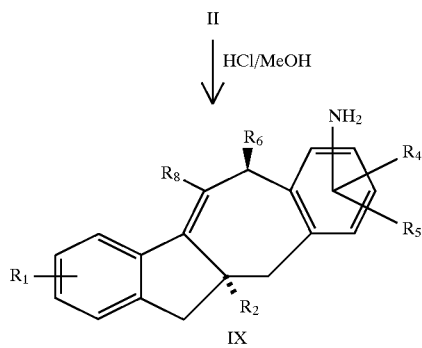

Those amino compounds having a saturated seven membered ring are prepared in a similar manner using compounds IIIa and IIIb as the starting materials.

The amino compounds prepared above are diazotized to form the corresponding diazonium salts by means of a Sandmeyer reaction. The diazonium group can then be displaced with halogen using, for example, copper chloride or copper bromide, to form those compounds wherein $R_3$ is halo.

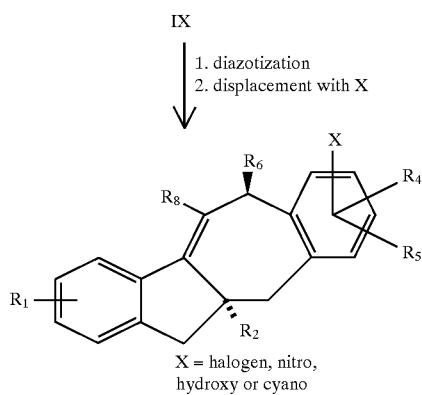

Those compounds having a saturated seven membered ring are prepared in a similar manner using compound III as the starting material.

Reaction of compound XXI with an oxidizing agent such as sodium hypobromite causes the alkyl carbonyl group to be replaced by a carboxyl group to yield those compounds wherein $R_3$ is a carboxyl group.

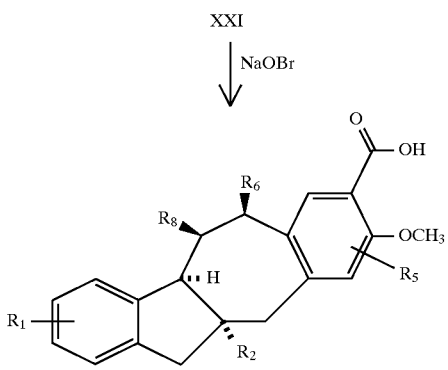

Reaction of compound II, wherein $R_6$ is hydrogen, with an oxidizing agent such as 1,3-dichloro-5,6-dicyano-1,4-benzoquinone or chloranil in a suitable solvent such as aqueous acetic acid or propionic acid, for example, results in the corresponding compound wherein $R_6$ and $R_7$ combine to form a carbonyl group. The carbonyl group is converted to an olefin by reaction with an alkyllithium compound such as methyl or propyl lithium, for example, in a suitable solvent such as ether, cyclohexane or THF and then treated with an acid such as hydrochloric acid, hydrobromic acid or p-toluenesulfonic acid. The olefin can be reduced to an alkyl group by hydrogenation in the presence of a suitable catalyst such as palladium or platinum on charcoal. If the hydrogenation step is carried out under about 30 psi with 10% Pd/C only the exocyclic double bond is reduced. If the hydrogenation is carried out at 50 psi both double bonds are reduced to form the compounds of this invention.

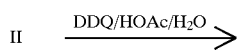
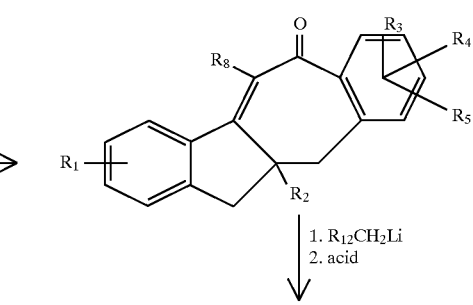

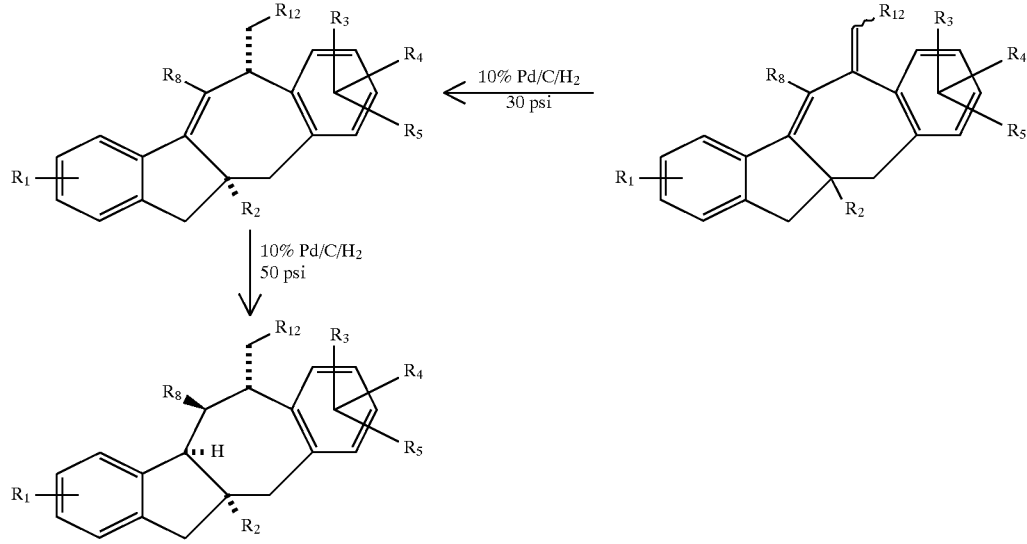

In the above reaction scheme $R_{12}$ is hydrogen or an alkyl group.

Compounds Va and Vb of the present invention having a carbonyl substituent on the saturated seven membered ring are prepared by reacting compounds IIa and IIb wherein $R_8$ is hydrogen first with a reducing agent such as diborane, isoamyl borane or borane methyl sulfide, for example, followed by the addition of hydrogen peroxide in the presence of a base such as sodium hydroxide or potassium hydroxide to form the corresponding alcohol (IV). Oxidation of the alcohol with a suitable oxidizing agent such as, for example, Jones reagent, Collins reagent, pyridinium dichromate or pyridinium chlorochromate, results in the formation of the corresponding ketones Va and Vb.

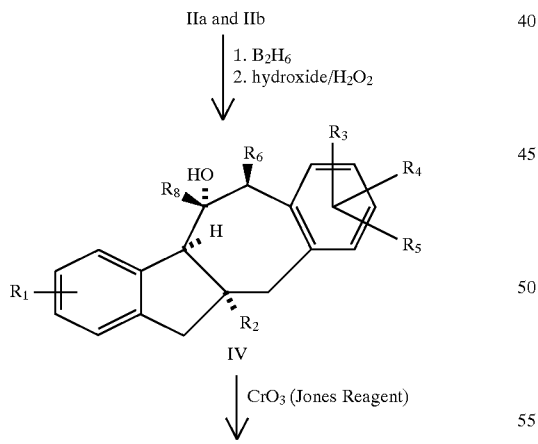

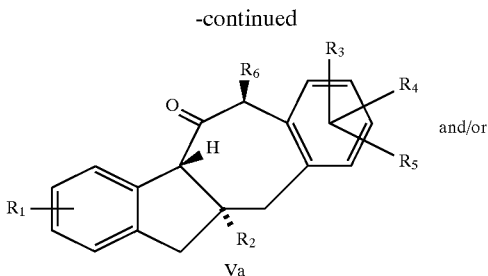

Reaction of the ketones (Va and Vb) with a reducing agent such as lithium aluminum hydride or sodium borohydride, for example, results in the formation of the corresponding alcohols.

Va         Vb

↓ Lithium aluminum hydride    ↓ Lithium aluminum hydride

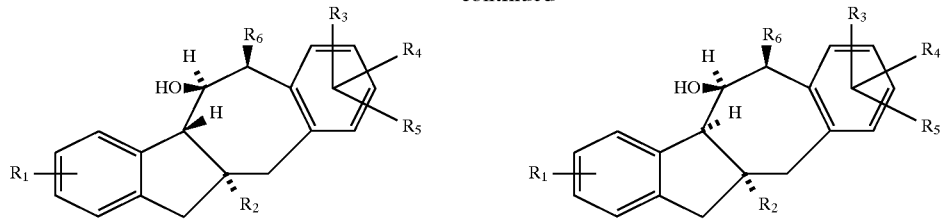

Compound II, wherein $R_3$ is hydroxy, can be converted to the corresponding ester by reaction with an appropriate alkyl anhydride such as, for example, acetic anhydride or with an acyl halide such as, for example, acetyl chloride in the presence of a base such as triethylamine, diisopropylethylamine or pyridine.

Reaction of compound IV, wherein $R_1$ is hydrogen or halogen, with a nitrating agent such as nitric acid in a suitable solvent such as acetic acid or propionic acid, results in the formation of the corresponding aromatic nitro derivative using dehydrating agents such as acetic anhydride. The hydroxy group of the seven membered ring is also esterified under these conditions. The alkyl radical on the alkoxy group is partially demethylated during the reaction to form the corresponding phenol. The formation of dinitro side products may also occur. (Illustrated structures are derived from IIb).

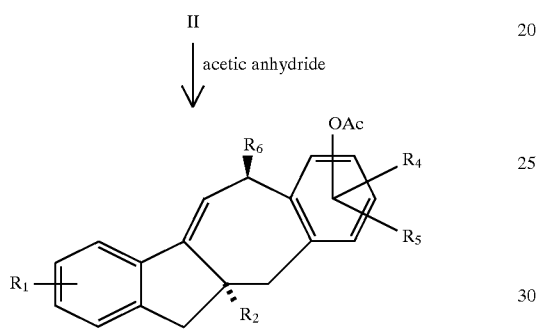

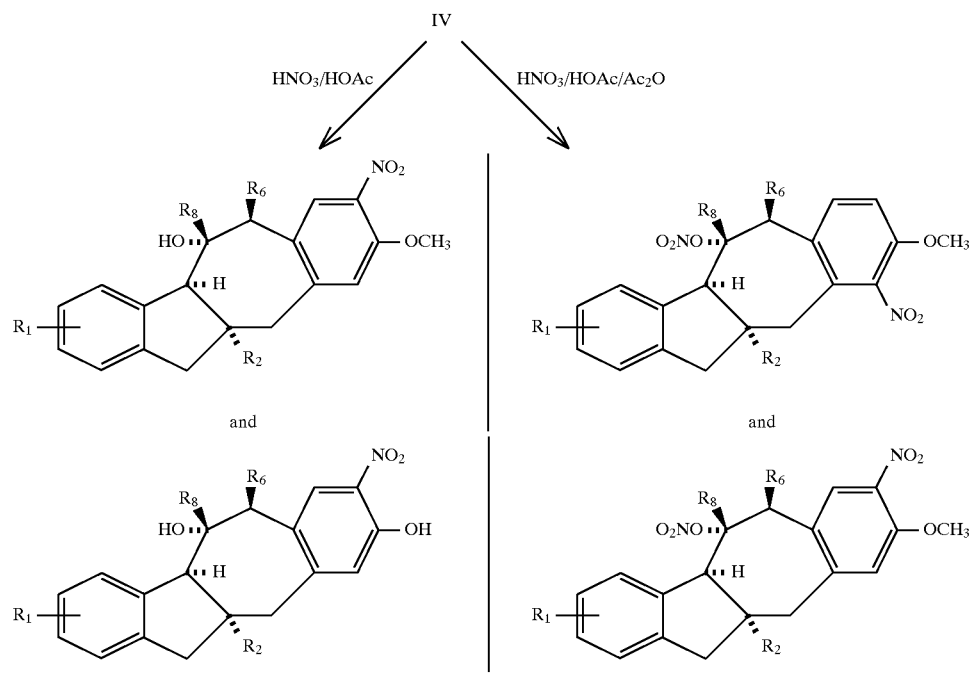

Phenol VI or compound III wherein $R_3$ is hydroxy, depending upon the reaction conditions employed, can be converted to the corresponding ether or ester derivative by first reacting the alcohol with a base such as sodium hydride or potassium hydride followed by reaction with the appropriate halide such as a dialkylphosphoryl halide, a dialkylaminoalkyl halide or a hydroxyalkyl halide such as, for example, dimethylaminoethyl chloride, diethylphosphoryl chloride or bromoethanol, or phenyltetrazoyl chloride. Those compounds having a phenyltetrazoyloxy group on the phenyl ring when reacted with a reducing agent such as hydrogen (Pd/C) lose the ester group to form the compounds having no substituent on the phenyl ring (D ring). Similar compounds can be prepared by carrying out a Birch reduction on the compounds having a dialkylphosphoryloxy group on the phenyl ring.

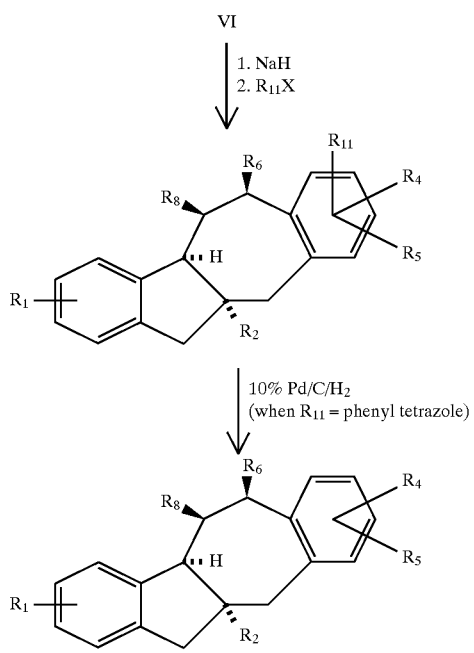

Compounds having a hydroxyalkyl group on the phenyl (D) ring can be prepared by reacting compounds XX with an organometallic compound such as a methyl or ethyl Grignard reagent, for example, under standard conditions for carrying out Grignard reactions. Reduction of the hydroxyalkyl derivatives using standard hydrogenolysis techniques results in compounds having an alkyl group on the D ring.

The indanone derivatives which are the starting materials for the preparation of the compounds of the present invention are either readily available or can be prepared by standard procedures known to those skilled in the art. For example, an appropriately substituted indanone is reacted with a base such as, for example, sodium hydride, and an alkyl halide, such as methyl iodide, to form the corresponding indanone wherein $R_2$ is alkyl.

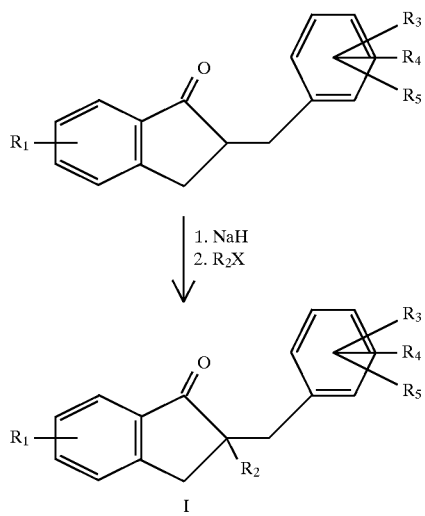

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g. intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions), or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. For parenterals, the carrier will usually comprise sterile water, though other ingredients may be employed, for example, to aid solubility or for preservative purposes; injectable suspensions may also be prepared, in which case appropriate liquid carriers, suspending agents and the like may be employed. The pharmaceutical compositions will generally contain a dosage unit, e.g. tablet, capsule, powder and the like, from about 0.1 µg/kg to about 20 mg/kg and preferably from about 0.1 µg/kg to about 10 mg/kg of the active ingredient.

The following examples describe the invention in greater detail and are intended to illustrate the invention but not to limit it.

BEST MODE FOR CARRYING OUT THE INVENTION

Melting point determinations were carried out on a Thomas Hoover capillary melting point apparatus and are uncorrected. All compounds had spectra (Elemental Analysis, IR, $^1$H NMR, MS) consistent with their assigned structures. The infrared spectra (IR) were recorded on a Perkin Elmer 1430 spectrometer and are expressed in reciprocal centimeters. Nuclear magnetic resonance (NMR) spectra for hydrogen atoms were measured in the indicated solvent with tetramethylsilane (TMS) as the internal standard on a Brucker WP-100 or a GE QE-300 spectrometer. The values are expressed in parts per million downfield from TMS. The elemental analyses were measured on a Perkin Elmer 2400 spectrometer and are expressed in percentage by weight of each element per total molecular weight. The mass spectra (MS) were determined on a Finnigan Mat 8230 or a Finnigan MAT INCOS 50, single stage, quadrupole using desorption chemical ionization techniques. All column chromatography was run using Silica Gel 60, 230–400 mesh and any appropriate commercially available solvent. Unless otherwise noted, the materials used in the examples were obtained from readily available commercial suppliers or synthesized by standard methods known to anyone skilled in the art of chemical synthesis.

The stereochemistry that is depicted in the schemes and designated in the examples is relative. No absolute determination of stereochemistry is claimed. When the substituent groups are on the same side of the ring system as $R_2$, the compound is an a. When the opposite case occurs the compound is b. The substituents groups, which vary between examples are assumed to be hydrogen unless otherwise noted. The general procedure according to Thompson (Tetrahedron Letters #52, pp 6489–6494, 1966) or Raju et al. (Indian J. Chem. B 26 (10) 914– 916 1987) was used in the synthesis of the starting materials listed in Table A.

TABLE A

| $R_1$ | $R_3$ | $R_4$ | $R_2$ |
|---|---|---|---|
| H | 3-$NH_2$ | H | Me |
| H | 3-OMe | H | n-Pr |
| H | 3-OMe | H | Et |
| H | 3-OMe | 5-OMe | Me |
| H | 3-OMe | H | n-Bu |
| H | 3-OMe | H | Me |
| 5-OMe | 3-OMe | H | n-Pr |
| 5-OMe | 3-OMe | H | Et |
| 5-OMe | 3-OMe | H | Me |
| 5-F | H | H | Me |
| 5-F | 3-OMe | H | n-Pr |

PROCEDURE 1

2-[(3-Aminophenyl)methyl]-2-methyl-1-indanone

2-[(3-Aminophenyl)methyl]indan-1-one (5.18 g, 22.0 mmol) in tetrahydrofuran (100 mL) was slowly added to a suspension of sodium hydride (2.20 g, 65.0 mmol), and tetrahydrofuran (100 mL) at room temperature and the mixture was stirred for 30 min. Methyl iodide (1.63 mL, 26.0 mmol) was added and the resulting mixture was stirred at room temperature for 5 h. Water (150 mL) was added, followed by methylene chloride (150 mL) and the resulting aqueous layer was washed with several portions of methylene chloride. The combined organic extracts were dried ($MgSO_4$), filtered and concentrated in vacuo to give the title compound as a solid: mp 95°–98° C., MS MH+252.

PROCEDURE 2

2-[(3-Acetamidophenyl)methyl]-2-methyl-1-indanone

Acetic anhydride (41.75 mL, 0.46 mol) was added to a stirred solution of 2-[(3-aminophenyl)methyl]-2-methyl-1-indanone (37.00 g, 0.147 mol) in ethyl acetate (800 mL) and this mixture was stirred at room temperature for 2 h. Saturated sodium bicarbonate (600 mL) was added to the resulting mixture, followed by successive washes of the aqueous layer with ethyl acetate. The combined organic extracts were washed with water (500 mL), dried ($MgSO_4$) and concentrated in vacuo to give the title compound as an oil: $^1$H NMR ($CDCl_3$) 7.7 (doublet, 1H), 7.55–7.15 (multiplet, 5H), 7.1 (doublet, 1H), 6.85 (doublet, 1H), 3.25 (doublet, 1H), 2.9 (doublet, 1H), 2.7 (doublet, 1H), 2.1 (singlet, 3H), 2.1 (doublet, 1H), 1.2 (singlet, 3H).

PROCEDURE 3

2-[(3-Acetamidophenyl)methyl]-2-methyl-1-allyl-2,3-dihydroindan-1-ol

2-[(3-Acetamidophenyl)methyl]-2-methyl-1-indanone (38.00 g, 0.13 mol) in tetrahydrofuran (1.1 L) was slowly added to allylmagnesium bromide (388.6 mL, 0.39 mol) in tetrahydrofuran (100 mL) at 0° C. and the resulting mixture was stirred for 3 h. Water (750 mL) and ethyl acetate (750 mL) were added to the reaction and the resulting aqueous layer was washed with several portions of ethyl acetate. The combined organic extracts were washed with water (500 mL), dried ($MgSO_4$) and concentrated in vacuo to give the title compound as a 50/50 mixture of diastereomers isolated as an oil: $^1$H NMR ($CDCl_3$) (multiplet, 5H), 7.0–6.75 (multiplet, 3H), 6.1–5.6 (multiplet, 2H), 5.2 (multiplet, 3H), 3.2–2.3 (multiplet, 4H), 2.13 (singlet, 3H), 1.0 (singlet, 1.5H), 0.85 (singlet, 1.5H).

EXAMPLE 1

9-Acetamido-6,11,11a,12-tetrahydro-6,11a-dimethyldibenz[a,f]azulene

Cpd. 83 p-Toluenesulfonic acid (0.25 g, 1.3 mmol) was added to a solution of 2-[(3-acetamidophenyl)methyl]-2-methyl-1-allyl-2,3-dihydroindan-1-ol (38.00 g, 113 mol) in toluene (3000 mL). The mixture was warmed to 80° C. on a rotary evaporator under reduced pressure for 1 h. The residual toluene was removed in vacuo and sat. $NaHCO_3$(aq) (500 mL) and ethyl acetate (1000 mL) were added to the residue. The aqueous layer was washed (2×) with ethyl acetate. The combined organic extracts were washed twice with $H_2O$ (400 mL), dried ($MgSO_4$) and concentrated in vacuo. The residue was purified by column chromatography on silica gel (750 kg) using ethyl acetate/hexane 25/75 as an eluent, to give the title compound as a solid: mp 228.5°–235° C.; MS MH+318.

EXAMPLE 2

2-Fluoro-6,11,11a,12-tetrahydro-9-methoxy-6,11a-dimethyldibenz[a,f]azulene

Cpd. 30

Allylmagnesium bromide (84 mL, 0.084 mol) was added to a solution of 5-fluoro-2-methyl-2-[(3-methoxyphenyl)

methyl]indanone (12.0 g, 0.0422 mol) in diethyl ether (150 mL) and the resulting mixture was stirred for 3 h at room temperature. The reaction mixture was quenched with water and then washed with successive portions of ether. The combined ether extracts were then washed with $H_2O$, dried ($MgSO_4$) and concentrated in vacuo to give an oil. This oil was dissolved in carbon tetrachloride (300 mL) and thionyl chloride (15 mL) was added. The resulting solution was heated to reflux for 15 min and cooled to room temperature. The solvent was evaporated under reduced pressure and the remaining thionyl chloride was removed by azeotropic distillation using carbon tetrachloride to leave a residue. Said residue was purified by column chromatography on silica gel using hexane/$CH_2Cl_2$:50/50 as an eluent and by recrystallization from ethanol to give a solid: mp 173°–175° C.

The following general procedure was used in the synthesis of the compounds listed in Table B.

An appropriate allyl Grignard (20 mM) was added to a suitably substituted indanone derivative I (10 mmol) in an appropriate solvent such as diethyl ether (36 mL) and the resulting mixture was stirred for 3 h at room temperature. The reaction mixture was quenched with water and then washed with successive portions of an organic solvent. The combined organic extracts were washed with $H_2O$, dried and concentrated in vacuo to give an oil. This oil was treated with either p-TsOH/toluene or $SOCl_2/CCl_4$, heated to reflux for 15 min and cooled to room temperature. The solvent was evaporated under reduced pressure and the remaining thionyl chloride was removed by azeotropic distillation using carbon tetrachloride to leave a residue. The residue was purified by any of the standard techniques which include column chromatography and recrystallization to give the desired material.

EXAMPLE 3

9-Acetamido-6,11a-dimethyl-4b,5,6,11,11a,12-hexahydrodibenz[a,f]azulene

Cpd.127

A solution of 9-acetamido-6,11,11a,12-tetrahydro-6,11a-dimethyldibenz[a,f]azulene (15.0 g, 0.0473 mol) in ethyl acetate (150 mL) was added to a suspension of palladium hydroxide (0.60 g) in ethyl acetate (100 mL). The mixture was hydrogenated at 50 psi for 48 h, followed by filtration through Celite 545 (25 g). The resulting solution was concentrated in vacuo to give the title compound as a white solid: $^1H$ NMR ($CDCl_3$) 7.3 (doublet, 1H), 7.2 (multiplet, 6H), 4.1 (quartet, 1H), 3.3 (multiplet, 2H), 2.9 (doublet, ¾H), 2.8 (doublet, ¼H), 2.6 (multiplet, 2H), 2.2 (singlet, 3H), 1.9 (multiplet, 1H), 1.7 (multiplet, 1H), 1.4 (doublet, ¾H), 1.3 (doublet, 2¼H), 0.9 (singlet, 2¼H), 0.6 (singlet, ¾H).

The following general procedure was used in the synthesis of the compounds listed in Table C. The a and b designations in the table designate the relative positions of the ring juncture H and $R_2$. In the alpha isomer both H and $R_2$ are on the same side of the molecule and in the beta isomer they are on opposite sides. Where the compounds were isolated as a mixture of diastereomers, the designation is a, b.

A solution of an appropriate azulene derivative II (10 mmol), in a suitable solvent such as ethyl acetate (30 mL) was added to a suspension of a suitable catalyst such as palladium hydroxide-carbon in an appropriate solvent (21.2 mL). The suspension was reduced on a Parr hydrogenator at 50 psi. The resulting mixture was filtered through Celite, and concentrated in vacuo. This residue was purified using any of the standard techniques which include column chromatography and recrystallization to give the desired derivatives IIIa or IIIb.

TABLE B

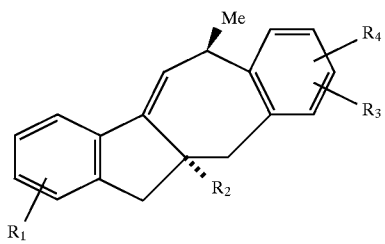

| Cpd. | $R_1$ | $R_2$ | $R_3$ | $R_4$ | mp °C. | C | H | N | Empirical |
|---|---|---|---|---|---|---|---|---|---|
| 3 | H | Me | 9-OMe | H | 128–130 | 86.67 | 8.62 | | C21H22O |
| 4 | 2-OMe | Me | 9-OMe | H | 149–151 | 82.33 | 7.27 | | C21H22O2 |
| 5 | 2-OMe | Me | 9-OMe | H | 169–170 | 82.60 | 7.38 | | C22H24O2 |
| 7 | H | Me | 7-OMe | H | 184–185 | 86.71 | 7.67 | | C21H22O |
| 11 | H | Me | 7-OMe | 9-OMe | 192–195 | 82.22 | 7.58 | | C22H24O2 |
| 17 | H | Et | 9-OMe | H | 78–81 | 86.78 | 8.25 | | C22H24O |
| 22 | 2-OMe | Et | 9-OMe | H | 65–69 | 82.38 | 7.81 | | C23H26O2 |
| 38 | H | n-Pr | 9-OMe | H | oil | 84.88 | 8.72 | | C23H26O |
| 42 | 2-OMe | n-Pr | 9-OMe | H | oil | 86.64 | 7.82 | | C24H28O2 |
| 150 | H | n-Bu | 9-OMe | H | 70–72 | 78.32 | 7.26 | | C24H28O |
| 84 | H | n-Pr | 9-NHAc | H | 217–219 | 86.81 | 8.45 | 4.66 | C24H27NO |

TABLE C

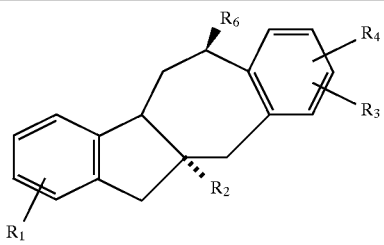

| Cpd | R₁ | R₂ | R₃ | R₄ | R₆ | mp °C. | C | H | N Empirical |
|---|---|---|---|---|---|---|---|---|---|
| 8a | H | Me | 9-OMe | H | Me | 95–97 | 86.17 | 8.40 | C21H24O |
| 23a, b | H | Et | 9-OMe | H | Me | 96–98 | 85.98 | 8.70 | C22H26O |
| 16b | H | Me | 9-OMe | H | Me | 74–75 | 85.92 | 8.33 | C21H24O |
| 35a, b | H | n-Pr | 9-OMe | H | H | oil | 84.69 | 7.10 | C22H26O |
| 47a | 2-F | Me | 9-OMe | H | Me | 70–71 | 84.74 | 8.78 | C21H23FO |
| 48a, b | H | n-Pr | 9-OMe | H | H | 94–95 | 66.25 | 6.98 | C23H28O |
| 54a | H | Me | 7-OMe | H | Me | 98–101 | 77.58 | 8.05 | C21H24O |
| 71a | 2-OMe | n-Pr | 9-OMe | H | H | 125.5–127 | 81.30 | 7.75 | C23H28O2 |
| 72a | 2-F | n-Pr | 9-OMe | H | H | 100.5–102 | 78.39 | 7.89 | C22H25FO |
| 73a | 2-F | n-Pr | 7-OMe | H | H | oil | 71.90 | 7.33 | C22H25FO |
| 86a | H | Me | 7-OMe | 9-OMe | Me | 99–100 | 75.78 | 7.13 | C22H26O2 |
| 87a | H | Me | 7-OAc | 9-OAc | Me | 121–123 | 84.77 | 7.66 | C24H26O4 |

EXAMPLE 4

2-Fluoro-4b,5,6,11,11a,12-hexahydro-9-hydroxy-6,11a-dimethyldibenz[a,f]azulene

Cpd. 128

2-Fluoro-4b,5,6,11,11a,12-hexahydro-9-methoxy-6,11a-dimethyldibenz[a,f]azulene (3.0 g, 9.7 mmol) was dissolved in methylene chloride (250 mL) and cooled to −78° C. in a dry ice-acetone bath. 1N Boron tribromide in $CH_2Cl_2$ (20 ml) was added and the reaction was allowed to warm to room temperature overnight. Excess boron tribromide was quenched with water and the reaction was washed with saturated sodium bicarbonate solution, and successive portions of water. The organic layer was dried ($MgSO_4$) and concentrated in vacuo to give an oil. The oil was purified by column chromatography on silica gel using 15% ethyl acetate in hexane to give the title compound as an oil: MS MH+311.

The following general procedure was used in the synthesis of the compounds listed in Table D Boron tribromide (10 mmol) was added to a solution of an appropriately substituted hexahydroazulene derivative (10 mmol) in methylene chloride (275 mL) at −78° C. After the addition was complete, the mixture was allowed to warm to room temperature for 12–72 h. The resulting mixture was partitioned between water and an appropriate organic solvent and the aqueous layer was washed with successive portions of ethyl acetate. The organic extracts were combined, dried (magnesium sulfate) and concentrated in vacuo to afford the desired compound.

TABLE D

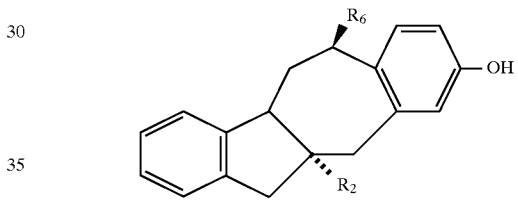

| Cpd. | R₆ | R₂ | mp °C. | C | H | Empirical |
|---|---|---|---|---|---|---|
| 12 | Me | Me | 89–91 | 85.96 | 8.15 | C20H22O |
| 40 | H | n-Pr | 152–153 | 85.52 | 7.21 | C21H24O |
| 46 | Me | Et | 106–109 | 81.34 | 7.80 | C21H24O |

EXAMPLE 5

9-Acetoxy-6-methyl-11a-methyl-6,11,11a,12-tetrahydrodibenz[a,f]azulene

To a solution of 9-hydroxy-6,11,11a-dimethyl-6,11,11a,12-tetrahydrodibenz[a,f]azulene (0.5 g, 0.0018 mol) and triethylamine 0.75 mL, 0.0054 mol.) in tetrahydrofuran (20 mL) was added dropwise acetyl chloride (0.2 mL, 0.0027 mol.). After stirring for 30 min. the reaction was quenched with water (0.5 mL) and diluted with 1N HCl (50 mL). The resulting mixture was extracted with ethyl acetate (2×100 mL) and the combined organic layers were washed with 1N HCl (100 mL) and then with water(2×100 mL). The organic layer was dried ($MgSO_4$) and evaporated to give a solid. Trituration of this solid with methanol gave an analytical sample, mp 131°–133° C., $^1H$ NMR ($CDCl_3$) 7.35–7.38 (multiplet, 1H), 7.11–7.22 (multiplet, 4H), 6.89–6.90 (doublet, 1H), 6.87 (singlet, 1H), 6.01–5.99 (doublet, 1H), 3.79–3.67 (multiplet, 1H), 3.45–3.42 (doublet, 1H), 3.01–2.96 (doublet, 1H), 2.81–2.76 (doublet, 1H), 2.66–2.71 (doublet, 1H), 2.29 (singlet, 3H), 1.42–1.40 (doublet, 3H), 0.86 (singlet, 3H).

The following general procedure was used in the synthesis of the compounds listed in Tables E and F.

To a solution of an appropriately substituted hydroxy azulene derivative (1.0 mM) and triethylamine (3.0 mM) in a suitable solvent (10 mL) was added dropwise an appropriate acyl halide (2.0 mM). The reaction was stirred for 30 min and then quenched with water (0.25 mL). After diluting with 1N HCl (25 mL) the mixture was extracted with several portions of an organic solvent. The combined organic layer was washed with water, dried and concentrated in vacuo. This residue was purified using any of the standard techniques which include column chromatography and/or recrystallization to give the desired azulene derivatives.

TABLE E

| Cpd. | $R_2$ | $R_3$ | mp °C. | C | H | Empirical |
|---|---|---|---|---|---|---|
| 50 | n-Pr | 9-OAc | oil | 81.53 | 8.74 | C23H26O2*¼H2O |
| 108 | Me | 7-OAc | 119–120 | 86.26 | 8.01 | C21H22O2 |

TABLE F

| Cpd. | $R_1$ | mp °C. | C | H | Empirical |
|---|---|---|---|---|---|
| 113 | 2-F | 191–192 | 82.23 | 6.54 | C21H19FO2 |
| 117 | 2-OMe | 175–176 | 85.81 | 7.71 | C22H22O3 |

EXAMPLE 6

8-Acetyl-4b,5,6,11,11a,12-hexahydro-6,11a-dimethyl-9-methoxydibenz[a,f]azulene

Cpd. 61

9-Methoxy-6,11a-dimethyl-4b,5,6,11,11a,12-hexahydrodibenz[a,f]azulene (5.0 g, 17.1 mmol) was stirred with acetic anhydride (7 mL, 68.6 mmol) and boron trifluoride etherate (1 mL, 8.1 mmol) in methylene chloride (150 mL) for 16 h. The solution was washed with water and the organic layers were dried (MgSO$_4$) and concentrated in vacuo to give an oil. Said oil was purified by column chromatography on silica gel using ethyl acetate/hexane (1:4) as an eluent to give the title compound as a solid: mp 174°–175.5° C.

The following general procedure was used in the synthesis of the compound listed in Table G An appropriately substituted azulene derivative IIb (10 mmol) was stirred with acetic anhydride (30–50 mmol) and boron trifluoride etherate (4.75 mmol) in a suitable solvent for 16 h. The solution was washed with water and the organic layer was dried (MgSO$_4$) and concentrated in vacuo to give a residue. Said residue was purified by any of the standard techniques which include column chromatography and recrystallization to give the desired compound.

TABLE G

| Cpd. | $R_3$ | $R_4$ | mp °C. | C | H | Empirical |
|---|---|---|---|---|---|---|
| 44 | 9-OMe | 8-Ac | 157–158 | 77.15 | 7.20 | C23H24O2 |

EXAMPLE 7

6,11a-Dimethyl-2-fluoro-8-nitro-9-methoxy-4b,5,6,11,11a,12-hexahydrodibenz[a,f]azulene ¼ Hydrate Cpd. 65

Concentrated nitric acid (2.0 mL, 31.8 mmol) was added to a solution of 2-fluoro-4b,5,6,11,11a,12-hexahydro-9-methoxy-6,11a-dimethyldibenz[a,f]azulene (1.0 g, 3.2 mmol) in acetic acid (20 mL). The solution was heated to 40° C. for one minute and then cooled to room temperature. The reaction was neutralized with saturated sodium bicarbonate solution and extracted into diethyl ether. The combined organic layers were washed with water, dried (MgSO$_4$) and concentrated in vacuo to give an oil. Purification by column chromatography (silica gel) using ethyl acetate/hexane (1:4) as an eluent gave two major products. The second compound off the column was found to be the title compound, obtained as a light yellow oil: MS MH+356.

The following general procedure was used in the synthesis of the compounds listed in Table H.

Nitric acid (10.0 mmol) was added to a solution of an appropriately substituted azulene derivative (II: 1.0 mmol) in acetic acid (6.6 mL) at room temperature. After addition was complete the reaction was stirred at room temperature for two hours. Saturated aqueous sodium bicarbonate and a suitable organic solvent were added to the reaction mixture; and the resulting aqueous layer was washed with successive portions of a suitable organic solvent. The organic extracts were combined, dried and concentrated in vacuo. The residue was purified by any of the standard techniques which include column chromatography and recrystallization to give the desired material.

TABLE H

| Cpd. | R₃ | R₄ | mp °C. | C | H | Empirical |
|---|---|---|---|---|---|---|
| 91 | 8-NO$_2$ | 9-NAc | oil | 71.56 | 6.32 | C22H24N2O3 |
| 102 | 9-OMe | 8-NO$_2$ | 90–94 | 56.38 | 4.94 | C21H23NO3 |

EXAMPLE 8

4b,5,6,11,11a,12-Hexahydro-9-hydroxy-6,11a-dimethyl-8,10-dinitrodibenz[a,f]azulene and 4b,5,6,11,11a,12-Hexahydro-9-methoxy-6,11a-dimethyl-8-nitro-dibenz[a,f]azulene

Cpd. 101

To a solution of 9-methoxy-6,11a-dimethyl-4b,5,6,11,11a,12-hexahydrodibenz[a,f]azulene (2.6 g, 8.9 mol) in acetic acid (250 mL) was added concentrated nitric acid (6 mL), followed by acetic anhydride (6 mL).

The solution was stirred for 1 h, and the resulting solution was poured into water. This mixture was stirred for 1 h and extracted into methylene chloride. The combined organic layer was washed with sucessive portions of water, dilute sodium bicarbonate and water. The organic layer was dried (MgSO$_4$) and concentrated in vacuo to an oil. Toluene was added, and the mixture was azeotropically distilled to remove any remaining acetic acid. The residue was purified by column chromatography on silica gel eluting with ethyl acetate/hexane (2:3). The first product off the column, 4b,5,6,11,11a,12-hexahydro-9-methoxy-6,11a-dimethyl-8-nitro-dibenz[a,f]azulene, was isolated as a crystalline solid, mp 90°–94° C. The second product off the column, 4b,5,6,11,11a,12-hexahydro-9-hydroxy- 6,11a-dimethyl-8,10-dinitrodibenz[a,f]azulene was recrystallized from ethyl acetate/hexane to give pure product as a crystalline solid: mp 156°–157° C.

EXAMPLE 9

5-(6,11a,-Dimethyl-9-methoxy-8-nitro-4b,5,6,11,11a,12-hexahydro)dibenz[a,f]azulenyl nitrate ester and 5-(6,11a-Dimethyl-9-methoxy-10-nitro-4b-5,6,11,11a,12-hexahydro)dibenz[a,f]azulenyl nitrate ester

Cpd. 81 and Cpd. 82

Concentrated nitric acid (20 mL) was added to a solution of 6,11a-dimethyl-5-hydroxy-9-methoxy-4b,5,6,11,11a,12-hexahydrodibenz[a,f]azulene (8.0 g, 26 mmol) in acetic acid (200 mL) and acetic anhydride (50 mL). The solution was stirred for 1 h and then poured into water. The resulting precipitate was filtered and purified by column chromatography on silica gel using ethyl acetate/hexane (2:3) as an eluent. The first product off the column was identified as the 10-nitro-5-nitrate ester of the starting material, and was isolated as colorless crystals mp 190°–192° C. The second product off the column was the 8-nitro-5-nitrate ester of the starting material, which was isolated as a solid: mp 198°–200° C.

EXAMPLE 10

6,11a-Dimethyl-5,9-dihydroxy-8-nitro-4b,5,6,11,11a,12-hexahydrodibenz[a,f]azulene and 6,11a-Dimethyl-5-hydroxy-9-methoxy-8-nitro-4b,5,6,11,11a,12-hexahydrodibenz[a,f]azulene

Cpd. 24 and Cpd. 25

Concentrated nitric acid (0.5 mL) was added to a solution of 6,11a-dimethyl-5-hydroxy-9-methoxy-4b,5,6,11,11a,12-hexahydrodibenz[a,f]azulene (2.0 g, 6.5 mmol) in acetic acid (50 mL) and the resulting solution was heated to 50° C. for 1.0 minute and cooled to room temperature. The mixture was poured into dilute sodium bicarbonate solution and extracted with diethyl ether. The combined organic layers were washed with water, dried (MgSO$_4$) and concentrated in vacuo to give an oil. This oil was purified by column chromatography on silica gel using 40% ethyl acetate/hexane as an eluent to give two major compounds. The first product that eluted off the column was the phenol, mp 173°–174° C. The second product was the methyl ether, which was recrystallized from ethyl acetate/hexane to give pure crystals, mp 152°–154° C.

EXAMPLE 11

9-Amino-6,11a-dimethyl-4b,5,6,11,11a,12-hexahydrodibenz[a,f]azulene

Cpd. 89

Concentrated hydrochloric acid (6 mL) was added to a solution of 9-acetamido-6,11a-dimethyl-4b,5,6,11,11a,12-hexahydrodibenz[a,f]azulene (9.00 g, 0.028 mol) in methanol (25 mL) and the resulting mixture was heated and stirred at reflux for 6 h. Cold 5N sodium hydroxide (500 mL) was added to the mixture followed by washing the aqueous layer with successive portions of ethyl acetate. The combined organic extracts were washed with water, dried (MgSO$_4$) and concentrated in vacuo to give the title compound as a mixture of diastereomers isolated as a light yellow oil:$^1$H NMR (CDCl$_3$) (75/25 mixture of diastereomers.) 7.15 (multiplet, 4H), 6.95 (doublet, 1H), 6.55 (doublet, 1H), 6.45 (singlet, 1H), 3.5 (singlet, 2H), 3.4 (multiplet, 2H), 2.95 (doublet, 1H), 2.7–2.4 (multiplet, 2H), 2.6 (doublet, 1H), 1.9 (multiplet, 2H), 1.3 (doublet, ¾H), 1.2 (doublet, 2¼H), 0.9 (singlet, 2¼H), 0.6 (singlet, ¾H).

The following general procedure was used in the synthesis of the compounds listed in Table I.

Concentrated hydrochloric acid (an excess) was added to a solution of an appropriately substituted acetamido derivative (10.0 mmol) in a suitable solvent such as methanol (9 mL) and the resulting mixture was heated and stirred at reflux for 6 h. Cold 5N sodium hydroxide (75 mL) was added to the mixture followed by washing the aqueous layer with successive portions of an organic solvent. The combined organic extracts were washed with water, dried and concentrated in vacuo. The residue was purified by any of the standard techniques which include column chromatography and recrystallization to give the desired material.

TABLE I

[Structure shown with R6, R3, R2 substituents on hexahydrodibenz[a,f]azulene skeleton]

| Cpd. | R$_6$ | R$_3$ | R$_2$ | mp °C. | C | H | Empirical Formula |
|---|---|---|---|---|---|---|---|
| 85 | Me | 9-NH$_2$ | n-Pr | 97–100 | 81.80 | 8.31 | C22H25N |
| 96 | H | 7-NH$_2$ | Me | oil | 82.56 | 6.29 | C19H21N |

EXAMPLE 12

6,11a-Dimethyl-9-fluoro-4b,5,6,11,11a,12-hexahydrodibenz[a,f]azulene

Cpd. 88

A solution of fluoroboric acid (48–50%) (1.437 mL) and water (0.60 mL) was added to a solution of 9-amino-6,11a-dimethyl-4b,5,6,11,11a,12-hexahydrodibenz[a,f]azulene (0.50 g, 2.0 mmol) dissolved in tetrahydrofuran (5 mL) and the resulting mixture was cooled to 0° C. A saturated aqueous solution of sodium nitrate (1 mL) was added dropwise to the cooled mixture at 0° C. and the reaction mixture was stirred at 5° C. for 30 min. The resulting precipitate was filtered, washed with methanol (5 mL) and ether (10 mL), and dried under reduced pressure. The solid residue was suspended in xylene (20 mL) and heated at reflux until the mixture turned very dark. The solvent was removed in vacuo and the resulting oil was purified by column chromatography on silica gel using methylene chloride/hexane 5:95 as an eluent to afford the title compound as a mixture of diastereomers isolated as a colorless oil: $^1$H NMR (CDCl$_3$) (75/25 mixture of diastereomers) 7.1 (multiplet, 5H), 6.9 (multiplet, 2H), 3.3 (multiplet 2H), 3.0 (doublet, 1H), 2.8 (doublet, 1H), 2.4 (multiplet, 2H), 2.0 (multiplet, 2H), 1.3 (multiplet, 2H), 1.4 (doublet, 2H), 1.3 (doublet, 2¼H), 0.9 (singlet, 2¼H), 0.6 (singlet, ¾H).

The following general procedure was used in the synthesis of the compounds listed in Table J.

A solution of an appropriate mineral acid (about 0.750 mL) and water (about 0.30 mL) was added to a solution of an appropriately substituted amino derivative (1 mmol), dissolved in a suitable solvent such as tetrahydrofuran (about 2.5 mL) and the resulting mixture was cooled to 0° C. A saturated aqueous solution of sodium nitrate (0.5 mL) was added dropwise to the cooled mixture at 0° C. and the reaction mixture was stirred at 0° C. for 30 min. The resulting precipitate was filtered, washed with a suitable solvent, and dried under reduced pressure. The solid residue was suspended in xylene (10 mL) and heated at reflux until the mixture turned very dark. The solvent was removed in vacuo and the residue was purified by any of the standard techniques which include column chromatography and recrystallization to give the desired material.

TABLE J

[Structure shown with R6, R3, R2 substituents on hexahydrodibenz[a,f]azulene skeleton]

| Cpd. | R$_6$ | R$_3$ | R$_2$ | mp °C. | C | H | Empirical Formula |
|---|---|---|---|---|---|---|---|
| 80 | Me | 9-Cl | n-Pr | 104–106 | 72.33 | 6.89 | C22H23Cl |
| 92 | Me | 9-Br | n-Pr | 105.5–109 | 82.92 | 6.99 | C22H23Br |
| 98 | H | 7-F | Me | 98–102.5 | 63.87 | 5.65 | C19H19F |
| 99 | Me | 9-I | n-Pr | 112.5–116 | 86.05 | 8.65 | C22H23I |

EXAMPLE 13

6,11,11a,12-Tetrahydro-9-methoxy-5,6,11a-trimethyldibenz[a,f]azulene

Cpd 10

Crotyl bromide (2.0 g, 0.015 mol) was added to a suspension of magnesium (0.4 g) in diethyl ether (100 mL) and allowed to stand for 2 h. 2-[(3-Methoxyphenyl)methyl]-2-methyl-1-indanone (2.0 g, 0.0075 mol) was added to the resulting Grignard solution and the reaction was stirred overnight. The reaction was quenched with water and the resulting organic layer was washed with several portions of water, dried (MgSO$_4$) and concentrated in vacuo. The residue was dissolved in toluene (100 mL) and p-toluenesulfonic acid (10 mg) was added. This mixture was stirred for 72 h and concentrated in vacuo to give a purple solid. This solid was dissolved into a minimum amount of boiling ethanol and ammonia was bubbled into this hot purple solution until said solution turned light yellow. Upon cooling, the title compound precipitated out of solution as colorless crystals: mp 158°–160° C.

EXAMPLE 14

7-Methoxy-11a-methyl-6,11,11a,12-tetrahydrodibenz[a,f]azulene and 9-Methoxy-11a-methyl-6,11,11a,12-tetrahydrodibenz[a,f]azulene Cpd. 1 and Cpd. 2

A solution of 2-[(3-methoxyphenyl]-2-methyl-1-indanone (1.0 g, 3.7 mmol) in 2 mL of diethyl ether was added via syringe at −120° C. to a solution of vinyl lithium (7.5 mmol) (Neumann and Seebach 1976 *Tet. Letters.* No. 52, 4839–4842). The mixture was allowed to warm slowly to 25° C. and quenched with water. The organic layer was washed with several portions of water, dried (MgSO$_4$) and concentrated in vacuo. The resulting oil was purified by column chromatography on silica gel using 15% ethyl acetate/hexane as an eluent. After removal of solvent the resulting oil was dissolved in methylene chloride (50 mL) and thionyl chloride (2.0 mL) was added. The reaction mixture was stirred for 5 h and quenched with aqueous sodium bicarbonate (sat) (20 mL), washed with water (3×50 mL), dried (MgSO$_4$) and concentrated in vacuo. The residue was purified by column chromatography using silica gel and eluting with 10% methylene chloride in hexane to give the title compounds. The first product that eluted off the column was the 7-methoxy compound, mp 134°–135° C.; and the second product that eluted off the column was the 9-methoxy compound, mp 135°–137° C., $^1$H NMR (CDCl$_3$) 7.34–7.31 (multiplet, 1H), 7.25–7.14 (m, 3H), 7.04 (doublet, 1H), 6.74 (d,1H), 6.69 (doublet of doublets, 1H), 6.05 (dd, 1H), 3.88–3.80 (multiplet, 1H), 3.80 (singlet, 3H), 3.35–3.48 (m, 2H), 2.99 (d, 1H), 2.76 (d, 1H), 2.70 (doublet, 1H), 0.80 (s, 3H).

The following general procedure was used in the synthesis of the compounds listed in Table K.

A solution of an appropriately substituted indanone derivative I (1 mmol) in a suitable solvent such as diethyl ether (0.55 mL) was added via syringe at −120° C. to a solution of vinyl magnesium bromide or vinyl lithium (2.0 mmol) (Neumann and Seebach 1976 *Tet. Letters*. No. 52, 4839–4842). The mixture was allowed to warm slowly to 25° C. and quenched with water. The organic layer was washed with several portions of water, dried and concentrated in vacuo. The resulting oil was purified by column chromatography, and was dissolved in a suitable solvent (13.5 mL) and thionyl chloride (0.54 mL) was added. The reaction mixture was stirred for 5 h and quenched with aqueous sodium bicarbonate (sat) (20 mL), washed with water, dried and concentrated in vacuo. The residue was purified by any of the standard methods which include column chromatography and recrystallization to give the desired compound.

vacuo. The resulting residue was dissolved in toluene (100 mL) and p-toluenesulfonic acid (~10 mg) was added. The solution was heated to reflux for one hour and concentrated in vacuo. The resulting purple oil was purified by column chromatography on silica gel using methylene chloride/hexane (1:7) (that was treated with conc. ammonium hydroxide) as an eluent. The first compound off the chromatrography column was the 7-methoxy product, mp 153°–154° C., $^1$H NMR (CDCl$_3$) 7.26 (doublet, 1H), 7.11 (triplet, 1H), 6.75 (multiplet, 4), 5.92 (doublet doublets, 1H), 4.07 (d, d 1H), 3.82 (singlet, 3H), 3.79 (singlet, 3H), 3.79 (multiplet, 1H), 3.41 (multiplet, 2H), 2.95 (doublet, 1H), 2.80 (doublet, 1H), 2.65 (doublet, 1H), 0.81 (singlet, 3H); and the second compound off the column was the 9-methoxy product, mp 149°–151° C., $^1$H NMR (CDCl$_3$) 7.27 (doublet, 1H), 7.04 (doublet, 1H), 6.76–6.65 (multiplet, 4H), 5.91 (dd, 1H), 3.81 (multiplet, 1H), 3.80 (singlet, 3H), 3.79 (singlet, 3H), 3.45 (doublet, 1H), 3.35 (multiplet, 1H), 2.96 (doublet, 1H), 2.71 (doublet, 1H), 2.65 (doublet, 1H), 0.79 (singlet, 3H).

EXAMPLE 16

6,11a-Dimethyl-5-hydroxy-9-methoxy-4b,5,6,11,11a,12-hexahydrodibenz[a,f]azulene (α—OH)

Cpd. 13

A solution of 9-methoxy-6-methyl-11a-methyl-6,11,11a,12-tetrahydrodibenz[a,f]azulene (16.0 g, 55.1 mmol) in

TABLE K

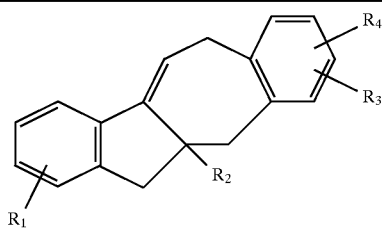

| Cpd. | $R_1$ | $R_3$ | $R_4$ | $R_2$ | mp | C | H | N | Empirical Formula |
|---|---|---|---|---|---|---|---|---|---|
| 6 | 2-OMe | 9-OMe | H | Me | 153–154 | 81.53 | 7.26 | | C21H22O2 |
| 9 | H | 7-OMe | 9-OMe | Me | 150–151 | 82.27 | 7.40 | | C21H22O2 |
| 27 | H | 9-OMe | H | n-Pr | 73–74 | 86.34 | 7.79 | | C22H24O |
| 29 | H | 7-OMe | H | n-Pr | 123–124 | 86.26 | 7.82 | | C22H24O |
| 37 | 2-OMe | 9-OMe | H | Et | 96–99 | 86.53 | 8.49 | | C22H24O½H2O |
| 43 | H | 9-OMe | H | Et | 108–110 | 82.82 | 7.07 | | C21H22O |
| 52 | H | 7-OMe | H | Et | 97–100 | 90.99 | 8.76 | | C21H22O |
| 56 | 2-F | 7-OMe | H | n-Pr | 125–126 | 81.68 | 7.26 | | C22H23FO |
| 57 | 2-F | 9-OMe | H | n-Pr | 112.5–114 | 80.49 | 7.02 | | C22H23FO |
| 67 | H | 9-OMe | H | n-Bu | 77–80 | 81.23 | 9.37 | 3.55 | C23H26O |
| 70 | H | 9-Me | H | Me | 118–119 | 78.28 | 8.23 | | C20H20 |
| 93 | H | 7-NAc | H | Me | 182–184.5 | 82.97 | 7.17 | 4.39 | C21H21NO |
| 95 | H | 9-NAc | H | Me | 216–219.5 | 86.66 | 8.23 | 5.40 | C21H21NO |

EXAMPLE 15

6,11,11a,12-Tetrahydro-2,7,dimethoxy-11a-methyl-benz[a,f]azulene and 6,11,11a,12-Tetrahydro-2,9-dimethoxy-11a-methyl-dibenz[a,f]azulene Cpd. 129 and Cpd. 34

1N Vinyl magnesium bromide (5.0 mL, 0.005 mol) was added to a solution of 2-methyl-2-[(3-methoxyphenyl)methyl]-5-methoxy-1-indanone (1.0 g, 3.4 mmol) in diethyl ether (50 mL). The mixture was stirred for 3 h and quenched with water. The resulting organic layer was washed with several portions of water, dried (K$_2$CO$_3$) and concentrated in dimethoxyethane (150 mL) was heated to reflux. 1N Diborane in tetrahydrofuran (65 mL, 6.5 mmol) was added dropwise at a fast rate and the resulting mixture was heated at reflux for another ½ h. The reaction was cooled to room temperature and water (7 mL) was cautiously added, followed by 1N sodium hydroxide (22 mL). 30% Hydrogen peroxide (8 mL) was added to the mixture and the resulting mixture was heated to 40° C. and immediately cooled to room temperature. The mixture was extracted with diethyl ether and the organic layer was washed with water. The organic layer was dried (MgSO$_4$) and concentrated in vacuo to give a solid. Trituration of said solid with hexane gave the title compound as a solid: mp 128°–130° C.

The following general procedure was used in the synthesis of the compounds listed in Table L.

A solution of an appropriate azulene derivative (10 mmol) in a suitable solvent (27 mmol) was heated to reflux. 1N Diborane in tetrahydrofuran (1.17 mmol) was added dropwise at a fast rate and the resulting mixture was heated at reflux for another ½ h. The reaction was cooled to room temperature and water was cautiously added, followed by 1N sodium hydroxide. 30% Hydrogen peroxide was added to the mixture and the resulting mixture was heated to 40° C. and immediately cooled to room temperature. The mixture was extracted with an appropriate solvent and the organic layer was washed with water. The organic layer was dried and concentrated in vacuo. The residue was purified by any of the standard techniques which include column chromatography, recrystallization and trituration to give the desired compounds.

TABLE L

| Cpd. | $R_1$ | $R_2$ | mp °C. | C | H | Empirical |
|---|---|---|---|---|---|---|
| 19 | 2-OMe | Me | 118–119 | 78.01 | 7.97 | C22H26O3 |
| 33 | H | Et | 146–148 | 79.74 | 7.88 | C22H26O2½H2O |
| 45 | 2-F | Me | 114–115 | 86.29 | 8.69 | C21H23FO2 |

EXAMPLE 17

6,11a-Dimethyl-9-methoxy-5-oxo-4b,5,6,11,11a,12-hexahydrodibenz[a,f]azulene

Cpd. 14

Jones reagent was added dropwise to a solution of 6,11a-dimethyl-5-hydroxy-9-methoxy-4b,5,6,11,11a,12-hexahydrodibenz[a,f]azulene (2.0 g, 6.5 mmol) in acetone (50 mL) until the solution turned green. The excess reagent was quenched with ethanol and the mixture was filtered through magnesium sulfate. Evaporation of the solvent in vacuo gave a solid which was recrystallized from ethanol to give the title compound as a single diastereomer, mp 122°–124° C., $^1$H NMR (CDCl$_3$) 7.19 (multiplet, 4H), 7.03 (doublet, 1H), 6.83 (double doublets, 1H), 6.70 (doublet, 1H), 3.83 (singlet, 3H), 3.79 (singlet, 1H), 3.64 (quartet, 1H), 2.95 (doublet, 1H), 2.93 (doublet, 1H), 2.64 (doublet, 1H), 2.56 (doublet, 1H), 1.38 (doublet, 3H), 0.96 (singlet, 3H). The filtrate was concentrated in vacuo to give an oil. Said oil was purified by column chromatography on silica gel using 5% ethyl acetate in hexane as an eluent to give the minor diastereomer of the product, mp 132°–133° C., $^1$H NMR (CDCl$_3$) 7.17 (multiplet, 3H), 7.05 (doublet, 1H), 6.96 (doublet, 1H), 6.72 (doublet doublets, 1H), 6.65 (doublet, 1H), 3.99 (quartet, 1H), 3.84 (singlet, 1H), 3.78 (singlet, 3H), 3.24 (doublet, 1H), 2.95 (doublet, 1H), 2.87 (doublet, 1H), 2.49 (doublet, 1H), 1.48 (doublet, 3H), 1.15 (singlet, 3H).

The following general procedure was used in the synthesis of the compounds listed in Table M.

Jones reagent was added dropwise to a solution of an appropriately substituted 5-hydroxy azulene derivative IV (1.0 mmol in acetone, 7.7 mL) until the solution turned green. The excess reagent was quenched with ethanol and the mixture was filtered through magnesium sulfate. Evaporation of the solvent in vacuo gave a solid which was purified by any of the standard techniques which include column chromatography and recrystallization to give the desired compounds.

TABLE M

| Cpd. | $R_6$ | mp °C. | C | H | Empirical |
|---|---|---|---|---|---|
| *75 | H | 198–200 | 78.12 | 9.98 | C21H22O3 |
| *76 | H | 107–109 | 78.23 | 7.22 | C21H22O3 |
| 77 | Me | 122–124 | 77.94 | 7.85 | C22C24O3 |

*Compounds 75 and 76 are diastereomers.

EXAMPLE 18

6,11a-Dimethyl-5-hydroxy-9-methoxy-4b,5,6,11,11a,12-hexahydrodibenz[a,f]azulene (β-OH)

Cpd. 64

Lithium aluminum hydride (50 mg, 1.35 mol) was added in portions to a solution of 6,11a-dimethyl-9-methoxy-5-oxo-4b,5,6,11,11a,12-hexahydrobenz[a,f]azulene (300 mg, 0.98 mol) in diethyl ether (25 mL). The excess lithium aluminum hydride was quenched with water and the diethyl ether layer diluted with additional diethyl ether (50 mL). The combined organic layer was washed with water (3×), dried (MgSO$_4$) and concentrated in vacuo to give a solid. This solid was crystallized from hexane and ethyl acetate to give the title compound as a solid: mp 159°–161° C.

The following general procedure was used in the synthesis of the compound listed in Table N.

Lithium aluminum hydride (1.3 mmol) was added in portions to a solution of an appropriately substituted oxo azulene derivative Va or Vb (1 mmol) in a suitable solvent. The excess lithium aluminum hydride was quenched with water and the organic layer was diluted with solvent. The combined organic layer was washed with water and dried and concentrated in vacuo to give a residue. Said residue was purified by any of the standard techniques which include column chromatography and recrystallization to give the desired compounds.

TABLE N

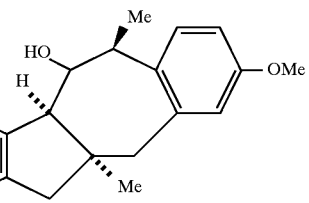

| Cpd. | R₁ | mp °C. | C | H | Empirical |
|---|---|---|---|---|---|
| 78 | OMe | 108–110 | 82.40 | 7.89 | C22H26O3 |

EXAMPLE 19
2-Fluoro-4b,5,6,11,11a,12-hexahydro-9-hydroxy-6,11a-dimethyldibenz[a,f]azulene Cpd. 130

2-Fluoro-4b,5,6,11,11a,12-hexahydro-9-methoxy-6,11a-dimethyldibenz[a,f]azulene (3.0 g, 9.7 mmol) was dissolved in methylene chloride (250 mL) and cooled to −78° C. in a dry ice-acetone bath. 1N Boron tribromide (10 mL) was added and the reaction was allowed to warm to room temperature overnight. Excess boron tribromide was quenched with water and the reaction was washed with saturated sodium bicarbonate solution, and successive portions of water. The organic layer was dried (MgSO₄) and concentrated in vacuo to give an oil. The oil was purified by column chromatography on silica gel using 15% ethyl acetate in hexane to give the title compound as an oil: MS MH+311.

EXAMPLE 20
9-(2-Fluoro-6,11,11a,12-tetrahydro-6,11a-dimethyl)-dibenz[a,f]azulenyl diethyl phosphoric acid Cpd. 49

A solution of 2-fluoro-4b,5,6,11,11a,12-hexahydro-9-hydroxy-6,11a-dimethyldibenz[a,f]azulene (1.0 g, 3.4 mmol) in tetrahydrofuran (50 mL) was added dropwise to pentane washed sodium hydride (60% in mineral oil: 0.4 g, 0.01 mol). Diethylchlorophosphate (0.7 g, 4.1 mmol) was added and the reaction was stirred for 0.5 h. The resulting mixture was diluted with ether, washed with water, dried (MgSO₄) and concentrated in vacuo. The residue was purified by column chromatography on silica gel using ethyl acetate/hexane (1:1) as an eluent to give the title compound as an oil: MSMH+433.

EXAMPLE 21
6,11a-Dimethyl-9-(N,N'-dimethylamino)ethoxy-2-fluoro-4b,5,6,11,11a,12-hexahydro-6,11a-dimethyldibenz[a,f]-azulene Cpd. 55

A solution of 2-fluoro-4b,5,6,11,11a,12-hexahydro-9-hydroxy-6,11a-dimethyldibenz[a,f]azulene (0.9 g, 3.1 mmol) in dimethylformamide (10 mL) was added to sodium hydride (60% in mineral oil: 0.3 g, 7.3 mmol). The reaction was stirred for 15 min and 2-dimethylaminoethyl chloride (0.88 gm, 0.0062 mol) was added. The mixture was heated to 50° C. for 16 h and cooled to room temperature. Water was added and the mixture was extracted with several portions of diethyl ether. The combined organic layer was washed with water, dried (K₂CO₃) and concentrated in vacuo to give an oil. Said oil was purified by column chromatography on silica gel using methanol and methylene chloride (1:9) as an eluent to give the title compound as a light yellow oil: MS MH+368.

The following general procedure was used in the synthesis of the compounds listed in Table O A solution of an appropriately substituted hydroxy azulene derivative VI (1.0 mM) in a suitable solvent (3.5 mL) was added to sodium hydride (60% in mineral oil: 2.1 molar equivalents). The reaction was stirred for 15 min and an appropriate alkylating agent (2 mmol) was added. The mixture was heated to 50° C. for 16 h and cooled to room temperature. Water was added and the mixture was extracted with several portions of an organic solvent. The combined organic layer was washed with water, dried and concentrated in vacuo. The residue was purified by column chromatography to give the desired compound.

TABLE O

| Cpd. | R₆ | R₃ | R₂ | mp °C. | C | H | Empirical |
|---|---|---|---|---|---|---|---|
| 51 | Me | 9-O(CH₂)₂NMe₂ | Me | oil | 86.64 | 7.60 | C24H31NO¼H2O |
| 66 | H | 9-O(CH₂)₂NEt₂ | n-Pr | oil | 85.66 | 7.82 | C27H37NO |

EXAMPLE 22
6,11a-Dimethyl-2-fluoro-9-(1-phenyl-5-tetrazolyl)-oxy-4b,5,6,11,11a,12-hexahydrodibenz[a,f]azulene Cpd. 63

A solution of 2-fluoro-4b,5,6,11,11a,12-hexahydro-9-hydroxy-6,11a-dimethyldibenz[a,f]azulene (1.0 g, 3.4 mmol) in dimethylformamide (10 mL) was added to a stirred suspension of pentane washed sodium hydride (60% in mineral oil) (0.4 g, 0.01 mol). After 15 minutes, 5-chloro-1-phenyl-1H-tetrazole (0.67 9, 3.7 mmol) was added and the resulting mixture was heated to 50° C. for 3 h and cooled to room temperature. The excess sodium hydride was quenched with water and the mixture extracted with diethyl ether. The combined organic layer was washed with water (3×50 mL), dried (MgSO$_4$) and concentrated in vacuo to give an oil. This oil was purified by column chromatography on silica gel using ethyl acetate/hexane (15:85) as an eluent to give the title compound as a foam: MS MH+441.

EXAMPLE 23

6,11a-Dimethyl-2-fluoro-4b,5,6,11,11a,12-hexahydrodibenz[a,f]azulene

Cpd. 69

A solution of 6,11a-dimethyl-2-fluoro-9-(1-phenyl-5-tetrazolyl)-oxy-4b,5,6,11,11a,12-hexahydrodibenz[a,f]azulene (0.5 g, 1.1 mmol) in tetrahydrofuran (60 mL) was added to 10% Pd-charcoal (100 mg) in a Parr bottle. The bottle was filled with hydrogen to 50 psi and shaken for 6 h. The mixture was filtered through Celite and the solvent was concentrated in vacuo to give an oil. The oil was dissolved in hexane and passed through a bed of silica gel (in a Pasteur pipet) using hexane as an eluent. Evaporation of the solvent gave the title compound as a clear oil: MS 356 (MH+).

EXAMPLE 24

6,11,11a,12-Tetrahydro-8-carboxy-9-methoxy-6,11a-dimethyldibenz[a,f]azulene

Cpd. 80

Sodium hypobromite was prepared in situ by first dissolving NaOH (1.6 g, 0.04 mol) in water (13 mL) and cooling to −5° C. Bromine (0.5 mL, 0.010 mol) was then added (dropwise) to this cooled solution, followed by the addition of dioxane (9 mL). The temperature of the freshly prepared hypobromite solution was kept at 0° C. A solution of 8-acetyl-4b,5,6,11,11a,12-hexahydro-6,11a-dimethyl-9-methoxydibenz[a,f]azulene (1.0 g, 3.0 mmol) in aqueous dioxane (53 mL, 77%) was cooled at 8° C. and stirred with a mechanical stirrer. The sodium hypobromite solution was added to the stirred solution and the temperature was kept at 10° C. for one hour. The mixture was then allowed to warm to room temperature and stirred for 3 h. The excess sodium hypobromite was destroyed by adding a solution of sodium bisulfite (0.5 g) in water (4 mL). The resulting mixture was heated to reflux for 15 minutes and acidified while hot with 2 mL of concentrated hydrochloric acid. Upon cooling, the mixture was extracted with diethyl ether. The combined organic extracts were washed with water, dried (MgSO$_4$) and concentrated in vacuo to give an oil. This oil was purified by column chromatography on silica gel using ethyl acetate/hexane (1:1) as an eluent to give the title compound as a solid: mp 153°–154° C.

EXAMPLE 25

6,11,11a,12-Tetrahydro-6-methenyl-9-methoxy-11a-methyldibenz[a,f]azulene

Cpd. 105

To a solution of 6,11,11a,12-tetrahydro-9-methoxy-11a-methyl-6-oxodibenz[a,f]azulene (2.0 g, 6.9 mmol) in diethyl ether (150 mL) was added 1.4N methyl lithium in diethyl ether (7 mL). The reaction mixture was stirred for 10 min and quenched with water. The diethyl ether layer was washed with successive washes of water, 1N hydrochloric acid and water, and dried over magnesium sulfate. Evaporation of the solvent in vacuo gave an oil. This oil was dissolved in methylene chloride and heated at reflux with 4 Å molecular sieves for 16 h. The mixture was filtered and the solvent removed in vacuo to give a solid. The solid was dissolved in methylene chloride and passed through a plug of silica gel. The solvent was removed in vacuo and the residue was recrystallized from methanol to give the title compound as a solid: mp 171°–173° C.

EXAMPLE 26

6,11,11a,12-Tetrahydro-9-methoxy-11a-methyl-6-oxodibenz[a,f]azulene

Cpd. 97

2,3-Dichloro-5,6-dicyano-1,4-benzoquinone (0.8 g, 3.6 mmol) was added to a stirred suspension of 9-methoxy-11a-methyl-6,11,11a,12-tetrahydrodibenz[a,f]azulene (1.0 g, 3.6 mmol) in acetic acid (45 mL) and water (5 mL). The reaction mixture was stirred for 2 h and an additional portion of 2,3-dichloro-5,6-dicyano-1,4-benzoquinone (0.8 g, 3.6 mmol) was added. The reaction mixture was stirred for another hour, poured into water (100 mL) and extracted with diethyl ether. The combined organic layers were washed with successive portions of 1N sodium hydroxide and water, dried (MgSO$_4$) and concentrated in vacuo. The residue was purified by column chromatography on silica gel using methylene chloride as an eluent followed by trituration with methanol to give the title compound as a solid: mp 122°–123° C.

EXAMPLE 27

6,11,11a,12-Tetrahydro-9-methoxy-6,11a-dimethyldibenz[a,f]-azulene

Cpd. 106

6,11,11a,12-Tetrahydro-6-methenyl-9-methoxy-11a-methyl-dibenz[a,f]azulene (0.5 g, 1.7 mmol) was suspended in tetrahydrofuran (150 mL) containing 10% palladium carbon (25 mg). The mixture was reduced at 30 psi on a Parr hydrogenator. After 16 h the mixture was filtered through celite and concentrated in vacuo. The residue was triturated with methanol to give a solid, which was recrystallized from methanol to give the title compound as a solid: mp 140°–142° C.

EXAMPLE 28

4b,5,6,11,11a,12-Hexahydro-7-methoxy-6,11a-dimethyldibenz-[a,f]azulene

Cpd. 109

7-Methoxy-11a-methyl-6,11,11a,12-tetrahydrodibenz[a,f]azulene (3.0 g, 0.0109 mol) was suspended in ethyl acetate (250 mL) containing palladium/calcium carbonate (100 mg). The mixture was reduced at 30 psi on the Parr hydrogenator. After 8 h the reaction was filtered through celite and concentrated in vacuo. Recrystallization of the resulting solid from methanol yielding the title compound as a solid: mp 127°–129° C.

EXAMPLE 29

4b,5,6,11,11a,12-Hexahydro-9-methoxy-6,11a-dimethyldibenz-[a,f]azulene

Cpd. 107

6,11,11a,12-Tetrahydro-6-methenyl-9-methoxy-11a-methyl-dibenz-[a,f]azulene (1.0 g, 3.5 mmol) was suspended in ethyl acetate (250 mL) containing palladium on carbon (10%, 200 mg). The mixture was reduced at 50 psi on the Parr hydrogenator over 3 h. The reaction was filtered through celite and concentrated in vacuo to give an oil. Trituration of said oil with methanol gave the title compound as a solid m.p. 93°–95° C.

EXAMPLE 30

6,11a,-Dimethyl-4b,5,6,11,11a,12-hexahydrodibenz [a,f]azulene

Cpd. 28

Small portions of sodium metal were added to a solution of 9-(6,11,11a,12-tetrahydro-6,11a-dimethyl)dibenz[a,f] azulenyl diethyl phosphoric acid (1.5 g, 36 mmol), liquid ammonia (75 mL) and ether (15 mL) until the characteristic blue color persisted for 15 min. The ammonia was allowed to evaporate and the resulting residue was extracted several times with hexane and the combined organic extracts were washed with water. The combined organic layer was dried with $MgSO_4$ and concentrated in vacuo. The residue was purified by column chromatography on silica gel using hexane as an eluent to give the title compound as an oil.

Anal. Calc'd for $C_{20}H_{22}$: C, 91.55; H, 8.45 Found: C, 91.51; H, 8.21

The following general procedure was used to synthesize the compound listed in Table P.

Small portions of sodium metal were added to a solution of an appropriately substituted dialkyl phosphoric acid derivative (10 mmol), liquid ammonia (20 mL and ether (4.2 mL) until the characteristic blue color persisted for 15 min. The ammonia was allowed to evaporate and the resulting residue was extracted several times with a suitable solvent followed by washing of the combined organic layer with water. The organic layer was dried with an appropriate drying agent and concentrated in vacuo. The residue was purified by column chromatography and/or recrystallization to give the desired compound.

TABLE P

| Cpd. | $R_2$ | mp °C. | C | H | Empirical |
|---|---|---|---|---|---|
| 53 | Et | oil | 85.98 | 8.27 | C21H24 |

EXAMPLE 31

Progestin Receptor Binding

The procedure used was essentially that of J. L. McGuire, C. D. Bariso and A. P. Shroff, *Biochemistry*, 13, 319 (1974).

Uteri from New Zealand rabbits (1.5 to 2.5 kg) were placed in a cold buffer A (0.01 mol Tris-HCl, pH 8.0, 0.001 mol EDTA, 0.25 mol sucrose). The uteri were minced, washed and homogenized in cold buffer A. The homogenate (2 g wet tissue/mL buffer) was centrifuged at 200,000×g for 1 h at 4° C. The high speed supernatant fraction was used as the receptor preparation.

A competitive binding assay was performed by mixing 3H-promegestone with the receptor preparation and adding a known amount of unlabeled compound. This mixture was incubated at 4° C. for 18 h. The compounds bound to the receptor were separated from those which were free in solution using dextran coated charcoal and the amount of isotope bound to the receptor was determined by scintillation counting. The extent of the compound's interaction with the receptor is measured as the percent reduction in the total isotope bound caused by the unlabeled test compound as compared to the control levels. The receptor screen consists of measuring the reduction in the total isotope bound caused by the unlabeled test compound at 0.1 mmol, 1 mmol and 10 mmol final concentrations. The data represented in Table R list the $IC_{50}$ values of a number of the compounds.

TABLE R

| Compound | $IC_{50}$ ($\mu$M) |
|---|---|
| 1 | 0.143 |
| 2 | 0.239 |
| 3 | 0.040 |
| 4 | 10.000 |
| 5 | 10.000 |
| 6 | 10.000 |
| 7 | 10.000 |
| 8 | 0.476 |
| 9 | 10.000 |
| 10 | 10.000 |
| 11 | 10.000 |
| 12 | 0.456 |
| 13 | 0.337 |
| 14 | 0.212 |
| 15 | 0.104 |
| 16 | 0.353 |
| 17 | 0.160 |
| 19 | 0.668 |
| 21 | 0.500 |
| 22 | 0.421 |
| 23 | 0.419 |
| 24 | 0.258 |
| 25 | 0.121 |
| 27 | 0.027 |
| 28 | 0.032 |
| 29 | 0.015 |
| 30 | 0.006 |
| 33 | 10.000 |
| 34 | 0.425 |
| 35 | 0.133 |
| 37 | 2.596 |
| 38 | 0.025 |
| 40 | 0.051 |
| 42 | 10.000 |
| 43 | 0.057 |
| 44 | 0.190 |
| 45 | 0.115 |
| 46 | 0.065 |
| 47 | 0.025 |
| 48 | 0.182 |
| 49 | 0.072 |
| 50 | 0.042 |
| 51 | 0.410 |
| 52 | 0.068 |
| 53 | 0.057 |
| 54 | 0.118 |
| 55 | 0.541 |
| 56 | 0.034 |
| 57 | 0.067 |
| 61 | 0.365 |
| 63 | 0.055 |
| 64 | 1.685 |
| 65 | 0.009 |
| 67 | 0.185 |
| 68 | 1.251 |
| 69 | 0.037 |
| 70 | 0.0420 |
| 71 | 0.4390 |

TABLE R-continued

| Compound | IC$_{50}$ ($\mu$M) |
|---|---|
| 72 | 0.100 |
| 73 | 0.100 |
| 74 | 0.199 |
| 75 | 0.555 |
| 76 | 10.000 |
| 77 | 10.000 |
| 78 | 10.000 |
| 80 | 10.000 |
| 81 | 0.082 |
| 82 | 0.099 |
| 83 | 1.969 |
| 84 | 0.161 |
| 85 | 0.019 |
| 86 | 1.675 |
| 87 | 0.729 |
| 88 | 0.034 |
| 89 | 0.137 |
| 90 | 0.032 |
| 91 | 0.115 |
| 92 | 0.139 |
| 93 | 10.000 |
| 95 | 1.768 |
| 96 | 0.034 |
| 97 | 10.000 |
| 98 | 0.0600 |
| 99 | 0.090 |
| 101 | 0.621 |
| 102 | 1.470 |
| 105 | 0.676 |
| 106 | 0.105 |
| 107 | 0.678 |
| 108 | 0.029 |
| 109 | 1.254 |
| 113 | 0.006 |
| 117 | 0.093 |

EXAMPLE 32

Reversal of Vaginal Atrophy Assay

Groups of mature, 150–175 g female rats are bilaterally ovariectomized under ether anesthesia. Seven days later, daily vaginal smears are obtained to verify complete castration. At least three consecutive diestrual smears indicate successful surgery. Rats are next injected subcutaneously on each of two successive days with 0.015 mg/kg estrone in 0.2 ml sesame oil per 200 g body weight to test their response to a standard estrogen.

Smears made on the subsequent two days should be estrual (presence of cornified cells) on at least one of these days. Animals that respond to estrogen stimulation are rested for about one week until vaginal smears once again indicate a diestrual state. Test compounds are administered orally once daily for two days and vaginal smears are obtained as with the estrogen priming dose, to determine the incidence of estrual smears. The data in Table S, is the dose in mg/kg, at which 2/2 rats show increased vaginal cornification in a number of compounds.

TABLE S

| Cpd. # | mg/kg |
|---|---|
| 30 | 25 |
| 29 | 12 |
| 47 | 25 |
| 38 | 25 |
| 27 | 25 |
| 28 | 25 |

TABLE S-continued

| Cpd. # | mg/kg |
|---|---|
| 69 | 25 |
| 3 | 10 |
| 40 | 10 |
| 54 | 25 |
| 17 | 25 |
| 67 | 25 |
| 2 | 10 |
| 12 | 10 |
| 68 | 5 |
| 5 | 10 |
| 7 | 10 |

EXAMPLE 33

Assay to Determine Effect of Compound on Uterine Proliferation (Clauberg Test)

The procedure used was essentially that of M. K. McPhail, *J. Physiology*, 83, 145 (1934). Groups of immature female white rabbits (750–950 g) were primed with a daily subcutaneous injection, for 6 days, with 5 micrograms of 17β-estradiol in 0.2 ml of sesame oil. Starting on the 7th day, they received the test compound daily for five days in the appropriate vehicle. The rabbits were sacrificed approximately 24 hours after the last administration, and the uteri were excised, cleaned and weighed. Portions of both uterine horns were fixed in 10% neutral formalin, sectioned at 6 $\mu$M and stained with hematoxylin and eosin. Progestational activity was assessed as in the McGinty Test. The evaluation for endometrial proliferation was made according to a McPhail Index. Each slide was graded for each rabbit on a 0 (no response)–4 (maximum response) scale. Cpd.#38 demonstrated a maximal response (4—McPhail Index) at 40 mg/kg when administered subcutaneously.

EXAMPLE 34

Assay to Demonstrate Ability to Increase Breast Cell Proliferation

This assay is used to measure the sex steroid effects of compounds. The activity of compounds in this assay is an indication of their potential use as replacements for naturally occuring hormones in individuals with sex hormone deficiencies.

T47D human breast carcinoma cells are grown in 96-well plates in phenol-red free nutrient media at 37° C. for 48 hours. Conditioned media is removed and replaced with fresh media containing test compounds dissolved in DMSO (0.1% final concentration) and the cells are incubated for an additional 18–20 hours at 37° C. [$^3$H]-thymidine is added to each well and allowed to incorporate into DNA for 4 hours. Unlabeled thymidine is then added to terminate the reaction, and the cultures are then washed, trypsinized and harvested. The amount of [$^3$H]-thymidine incorporated into DNA is determined by liquid scintillation. Data for each well are expressed as a percent above control level, which is set at 100%. The concentration at which maximal deviation from control is found and the magnitude of that percent deviation is reported. Table T lists the data for some of the compounds of this invention.

TABLE T

| Cpd. # | Concentration (μM) | % control |
|---|---|---|
| 27 | 0.7 | 224 |
| 30 | 7.0 | 204 |
| 38 | 5.0 | 189 |
| 43 | 1.0 | 151 |
| 45 | 5.0 | 191 |
| 53 | 1.0 | 50 |
| 63 | 10.0 | 94 |
| 70 | 10.0 | 173 |
| 78 | 0.1 | 112 |
| 81 | 10.0 | 56 |
| 85 | 4.0 | 215 |
| 88 | 10.0 | 187 |
| 124 | 0.08 | 462 |
| 113 | 0.71 | 470 |
| 122 | 1.0 | 105 |
| 123 | 0.79 | 387 |
| 117 | 5.0 | 160 |

What is claimed is:

1. A compound of the formula:

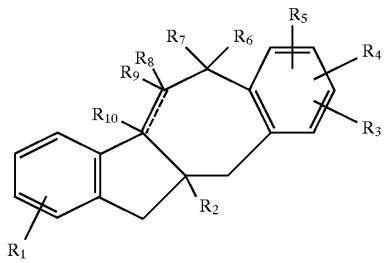

wherein $R_1$ is selected from the group consisting of hydrogen, halo, alkoxy ($C_1$–$C_6$) and hydroxy;

$R_2$ is alkyl ($C_1$–$C_6$);

$R_3$, $R_4$ and $R_5$ are selected from the group consisting of hydrogen, alkyl ($C_1$–$C_6$), alkoxy ($C_1$–$C_6$), benzyloxy, acyl ($C_2$–$C_6$), acyloxy ($C_2$–$C_6$), alkoxycarboxy wherein the alkoxy group has 1–5 carbon atoms, amino, acylamino ($C_2$–$C_6$), halo, nitro, hydroxy, cyano, alkylaminoalkoxy wherein the alkyl and alkoxy groups each contain 1–5 carbons, nitroso, dialkylphosphoryloxy, hydroxyalkyl ($C_1$–$C_6$), and phenyltetrazoyloxy;

$R_6$ and $R_7$ are selected from hydrogen, alkyl ($C_1$–$C_6$), hydroxy, and when taken together alkylene ($C_1$–$C_6$) and carbonyl;

$R_8$ is selected from hydrogen, alkyl, hydroxy or acyloxy ($C_2$–$C_6$);

$R_9$ and $R_{10}$ are hydrogen or together form a double bond, and $R_8$ and $R_9$ taken together form a carbonyl group, when $R_{10}$ is hydrogen.

2. A compound of claim 1 wherein $R_1$ is selected from the group consisting of hydrogen, halo, alkoxy and hydroxy; $R_2$ is alkyl; $R_3$, $R_4$ and $R_5$ are selected from the group consisting of hydrogen, alkyl, alkoxy, benzyloxy, acyl, acyloxy, amino, acylamino, halo, nitro, hydroxy, and alkylaminoalkoxy; $R_6$ and $R_7$ are hydrogen, alkyl, alkylene, hydroxy or carbonyl; $R_8$ is hydrogen, hydroxy or acyloxy; and $R_9$ and $R_{10}$ are hydrogen or together form a double bond.

3. A compound of claim 1 selected from the group consisting of: 9-acetamido-6,11,11a,12-tetrahydro-6,11a-dimethyldibenz[a,f]azulene; 2-fluoro-6,11,11a,12-tetrahydro-9-methoxy-6,11a-dimethyldibenz[a,f]azulene; 9-acetamido-6,11a-dimethyl-4b,5,6,11,11a,12-hexahydrodibenz[a,f]azulene; 2-fluoro-4b,5,6,11,11a,12-hexahydro-9-hydroxy-6,11a-dimethyldibenz[a,f]azulene; 2-fluoro -4b,5,6,11a,12-hexahydro-9-methoxy-6,11a-dimethyldibenz[a,f]azulene; and 9-acetoxy-6,11a-dimethyl-6,11,11a,12-tetrahydrodibenz[a,f]azulene.

4. A compound of claim 1 selected from the group consisting of:

8-acetyl-4b,5,6,11,11a,12-hexahydro-6,11a-dimethyl-9-methoxydibenz[a,f]azulene; 6,11a-dimethyl-2-fluoro-8-nitro-9-methoxy-4b,5,6,11a,12-hexahydrodibenz[a,f]azulene; 4b,5,6,11,11a,12-hexahydro-9-hydroxy-6,11a-dimethyl-8,10-dinitrodibenz[a,f]azulene; 4b,5,6,11,11a,12-hexahydro-9-methoxy-6,11a-dimethyl-8-nitrodibenz[a,f]azulene; 6,11a-dimethyl-9-methoxy-8-nitro-4b,5,6,11,11a,12-hexahydrodibenz[a,f]azulenyl nitrate; and 6,11a-dimethyl-9-methoxy-10-nitro-4b,5,6,11,11a,12-hexahydrodibenz[a,f]azulenyl nitrate.

5. A compound of claim 1 selected from the group consisting of:

6,11a-dimethyl-5,9-dihydroxy-8-nitro-4b,5,6,11,11a,12-hexahydrodibenz[a,f]azulene; 6,11a-dimethyl-5-hydroxy-9-methoxy-8-nitro-4b,5,6,11,11a,12-hexahydrodibenz[a,f]azulene; 9-amino-6,11a-dimethyl-4b,5,6,11,11a,12-hexahydrodibenz[a,f]azulene; 6,11a-dimethyl-9-fluoro-4b,5,6,11,11a,12-hexahydrodibenz[a,f]azulene; 6,11,11a,12-tetrahydro-9-methoxy-5,6,11a-trimethyldibenz[a,f]azulene; 7-methoxy-11a-methyl-6,11,11a,12-tetrahydrodibenz[a,f]azulene; and 9-methoxy-11a-methyl-6,11,11a,12-tetrahydrodibenz[a,f]azulene.

6. A method for inducing ovulation in a female which comprises administering to said female an effective amount of a compound of claim 1.

7. A method for controlling fertility in a female which comprises administering to said female an effective amount of a compound of claim 1.

8. A method for inhibiting spermatogenesis in a male which comprises administering to said male an effective amount of a compound of claim 1.

9. The process for preparing a compound of the formula:

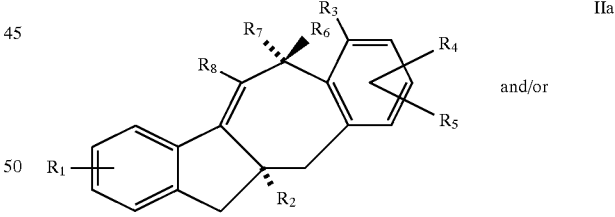

and/or

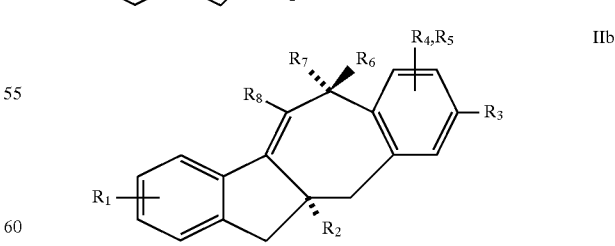

wherein $R_1$ is selected from hydrogen, halogen and alkoxy ($C_1$–$C_6$); $R_2$ is alkyl($C_1$–$C_6$); $R_3$, $R_4$ and $R_5$ are selected from alkyl($C_1$–$C_6$), acylamino($C_2$–$C_6$), alkoxy($C_1$–$C_6$) and hydroxy; and $R_6$, $R_7$ and $R_8$ are selected from hydrogen and alkyl($C_1$–$C_6$); which comprises reacting a substituted indanone of the formula:

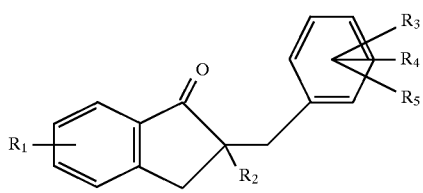

with a substituted metal halide in a suitable solvent and reacting the intermediate 2,3-dihydroindan-1-ol which forms with a cyclizing agent.

10. The process of claim 9 wherein the metal halide is selected from allylmagnesium bromide, vinyllithium bromide, vinylmagnesium bromide and crotyl magnesium bromide.

11. The process of claim 9 wherein the solvent is selected from tetrahydrofuran, diethyl ether and diisopropyl ether.

12. The process of claim 9 wherein the cyclizing agent is selected from p-toluenesulfonic acid, camphorsulfonic acid and thionyl chloride.

* * * * *